US010568613B2

(12) United States Patent
Zubiate et al.

(10) Patent No.: US 10,568,613 B2
(45) Date of Patent: Feb. 25, 2020

(54) MULTI-LINKED ENDOSCOPIC DEVICE WITH SPHERICAL DISTAL ASSEMBLY

(71) Applicant: Carnegie Mellon University, Pittsburgh, PA (US)

(72) Inventors: Brett Zubiate, Duxbury, MA (US); Howard Choset, Pittsburgh, PA (US); Amir Degani, Pittsburgh, PA (US); Anthony Kolb, East Longmeadow, MA (US); Kevin P. GilMartin, Braintree, MA (US); J. Christopher Flaherty, Topsfield, MA (US)

(73) Assignee: Carnegie Mellon University, Pittsburgh, PA (US)

( * ) Notice: Subject to any disclaimer, the term of this patent is extended or adjusted under 35 U.S.C. 154(b) by 319 days.

(21) Appl. No.: 15/175,499

(22) Filed: Jun. 7, 2016

(65) Prior Publication Data

US 2016/0361050 A1 Dec. 15, 2016

Related U.S. Application Data

(63) Continuation of application No. 13/062,659, filed as application No. PCT/US2009/056238 on Sep. 8, 2009, now Pat. No. 9,370,342.

(Continued)

(51) Int. Cl.
*A61B 5/01* (2006.01)
*A61B 17/00* (2006.01)
(Continued)

(52) U.S. Cl.
CPC ........ *A61B 17/00234* (2013.01); *A61B 1/008* (2013.01); *A61B 1/00052* (2013.01);
(Continued)

(58) Field of Classification Search
CPC .......... A61B 17/00234; A61B 1/00052; A61B 1/008; A61B 1/0055; A61B 1/04;
(Continued)

(56) References Cited

U.S. PATENT DOCUMENTS

| 992,509 A | 5/1911 | Kobzy |
| 2,238,660 A | 4/1941 | Santora |

(Continued)

FOREIGN PATENT DOCUMENTS

| CA | 2411530 A1 | 12/2001 |
| EP | 0686374 A2 | 12/1995 |

(Continued)

OTHER PUBLICATIONS

Shammas et al., "New Joint Design for Three-dimensional Hyper Redundant Robots," International Conference on Robots and Systems, Las Vegas, NV, Oct. 2003.

(Continued)

*Primary Examiner* — William J Levicky
*Assistant Examiner* — Shirley X Jian
(74) *Attorney, Agent, or Firm* — Fox Rothschild LLP

(57) ABSTRACT

A device for performing a procedure may include an elongate tube having a proximal end and a distal end and an adapted link having a proximal end and a distal end. The distal end may include a first mating surface, where the proximal end may be configured to attach to the distal end of the elongate tube. The device may also include a rotating link having a second mating surface configured to rotatably interface with the adapted link first mating surface.

14 Claims, 35 Drawing Sheets

Related U.S. Application Data

(60) Provisional application No. 61/094,606, filed on Sep. 5, 2008.

(51) Int. Cl.
*A61B 1/008* (2006.01)
*A61B 1/00* (2006.01)
*A61B 1/04* (2006.01)
*A61B 1/005* (2006.01)

(52) U.S. Cl.
CPC .............. *A61B 1/04* (2013.01); *A61B 1/0055* (2013.01); *A61B 2017/003* (2013.01); *A61B 2017/00314* (2013.01); *A61B 2017/00323* (2013.01)

(58) Field of Classification Search
CPC .... A61B 2017/003; A61B 2017/00323; A61B 2017/00314
See application file for complete search history.

(56) References Cited

U.S. PATENT DOCUMENTS

| | | |
|---|---|---|
| 3,060,972 A | 10/1962 | Sheldon |
| 3,190,286 A | 6/1965 | Stokes |
| 3,197,245 A | 7/1965 | Beer |
| 3,643,653 A | 2/1972 | Takahashi et al. |
| 4,364,535 A | 12/1982 | Itoh et al. |
| 4,548,373 A | 10/1985 | Komura |
| 4,686,963 A | 8/1987 | Cohen et al. |
| 4,805,477 A | 2/1989 | Akeel |
| 4,850,351 A | 7/1989 | Herman et al. |
| 4,884,916 A | 12/1989 | Johnson, III |
| 4,941,455 A | 7/1990 | Watanabe et al. |
| 4,946,122 A | 8/1990 | Ramsey et al. |
| 4,960,106 A | 10/1990 | Kubokawa et al. |
| 5,005,558 A | 4/1991 | Aomori |
| 5,142,932 A | 9/1992 | Moya et al. |
| 5,143,475 A | 9/1992 | Chikama |
| 5,251,611 A | 10/1993 | Zehel et al. |
| 5,253,832 A | 10/1993 | Bolas et al. |
| 5,257,618 A | 11/1993 | Kondo |
| 5,318,526 A | 6/1994 | Cohen |
| 5,327,905 A | 7/1994 | Avitall |
| 5,337,733 A | 8/1994 | Bauerfeind et al. |
| 5,375,588 A | 12/1994 | Yoon |
| 5,386,741 A | 2/1995 | Rennex |
| 5,415,158 A | 5/1995 | Barthel et al. |
| 5,467,763 A | 11/1995 | McMahon et al. |
| 5,472,017 A | 12/1995 | Kovalcheck |
| 5,483,951 A | 1/1996 | Frassica et al. |
| 5,514,157 A | 5/1996 | Nicholas et al. |
| 5,531,715 A | 7/1996 | Engelson et al. |
| 5,549,542 A | 8/1996 | Kovalcheck |
| 5,587,937 A | 12/1996 | Massie et al. |
| 5,605,543 A | 2/1997 | Swanson |
| 5,615,856 A | 4/1997 | Simington |
| 5,662,587 A | 9/1997 | Grundfest et al. |
| 5,695,501 A | 12/1997 | Carol et al. |
| 5,743,876 A | 4/1998 | Swanson |
| 5,749,828 A | 5/1998 | Solomon et al. |
| 5,752,973 A * | 5/1998 | Kieturakis .............. A61B 17/29 606/205 |
| 5,759,151 A | 6/1998 | Sturges |
| 5,810,716 A | 9/1998 | Mukherjee et al. |
| 5,836,199 A | 11/1998 | Loud |
| 5,843,152 A * | 12/1998 | Tu ...................... A61B 18/1492 607/122 |
| 5,868,760 A | 2/1999 | McGuckin, Jr. |
| 5,899,425 A * | 5/1999 | Corey, Jr. .............. A61B 17/02 248/276.1 |
| 5,907,487 A | 5/1999 | Rosenberg et al. |
| 5,947,996 A | 9/1999 | Logeman |
| 6,004,016 A | 12/1999 | Spector |
| 6,036,677 A | 3/2000 | Javier, Jr. et al. |
| 6,090,114 A | 7/2000 | Matsuno et al. |
| 6,197,017 B1 | 3/2001 | Brock et al. |
| 6,221,061 B1 | 4/2001 | Engelson et al. |
| 6,270,453 B1 | 8/2001 | Sakai |
| 6,277,064 B1 | 8/2001 | Yoon |
| 6,341,201 B1 | 1/2002 | Ishiguro et al. |
| 6,364,828 B1 | 4/2002 | Yeung et al. |
| 6,432,112 B2 | 8/2002 | Brock et al. |
| 6,450,104 B1 | 9/2002 | Grant et al. |
| 6,491,681 B1 | 12/2002 | Kunis et al. |
| 6,517,477 B1 | 2/2003 | Wendlandt |
| 6,554,844 B2 | 4/2003 | Lee et al. |
| 6,610,007 B2 | 8/2003 | Belson et al. |
| 6,623,448 B2 | 9/2003 | Slater |
| 6,638,266 B2 | 10/2003 | Wilson et al. |
| 6,682,493 B2 | 1/2004 | Mirigian |
| 6,692,485 B1 | 2/2004 | Brock et al. |
| 6,697,048 B2 | 2/2004 | Rosenberg et al. |
| 6,730,020 B2 | 5/2004 | Peng et al. |
| 6,743,239 B1 | 6/2004 | Kuehn et al. |
| 6,790,173 B2 | 9/2004 | Saadat et al. |
| 6,800,056 B2 | 10/2004 | Tartaglia et al. |
| 6,827,710 B1 | 12/2004 | Mooney et al. |
| 6,837,846 B2 | 1/2005 | Jaffe et al. |
| 6,837,847 B2 | 1/2005 | Ewers et al. |
| 6,858,005 B2 | 2/2005 | Ohline et al. |
| 6,869,396 B2 | 3/2005 | Belson |
| 6,890,297 B2 | 5/2005 | Belson |
| 6,899,673 B2 | 5/2005 | Ogura et al. |
| 6,907,298 B2 | 6/2005 | Smits et al. |
| 6,921,363 B2 | 7/2005 | Knowles |
| 6,953,222 B2 | 10/2005 | Larrick et al. |
| 6,960,162 B2 | 11/2005 | Saadat et al. |
| 6,960,163 B2 | 11/2005 | Ewers et al. |
| 6,963,792 B1 | 11/2005 | Green |
| 6,974,411 B2 | 12/2005 | Belson |
| 6,976,991 B2 | 12/2005 | Hebert et al. |
| 6,984,203 B2 | 1/2006 | Tartaglia et al. |
| 7,029,435 B2 | 4/2006 | Nakao |
| 7,041,052 B2 | 5/2006 | Saadat et al. |
| 7,044,907 B2 | 5/2006 | Belson |
| 7,087,013 B2 | 8/2006 | Belson et al. |
| 7,090,637 B2 | 8/2006 | Danitz et al. |
| 7,090,683 B2 | 8/2006 | Brock et al. |
| 7,108,688 B2 | 9/2006 | Jensen |
| 7,128,708 B2 | 10/2006 | Saadat et al. |
| 7,137,465 B1 | 11/2006 | Kerrebrock et al. |
| 7,169,141 B2 | 1/2007 | Brock et al. |
| 7,171,279 B2 | 1/2007 | Buckingham et al. |
| 7,182,731 B2 | 2/2007 | Nguyen et al. |
| 7,209,344 B2 | 4/2007 | Hillman et al. |
| 7,214,230 B2 | 5/2007 | Brock et al. |
| 7,232,434 B2 | 6/2007 | Suyama et al. |
| 7,250,027 B2 | 7/2007 | Barry |
| 7,278,253 B2 | 10/2007 | Wehler et al. |
| 7,322,935 B2 | 1/2008 | Palmer et al. |
| 7,338,505 B2 | 3/2008 | Belson |
| 7,387,046 B2 | 6/2008 | Ikeda et al. |
| 7,445,184 B1 | 11/2008 | Johnson |
| 7,484,351 B2 | 2/2009 | Harada et al. |
| 7,543,518 B2 | 6/2009 | Buckingham et al. |
| 7,566,300 B2 | 7/2009 | Devierre et al. |
| 7,670,284 B2 | 3/2010 | Padget et al. |
| 7,682,319 B2 | 3/2010 | Martin et al. |
| 7,811,277 B2 | 10/2010 | Boulais |
| 7,867,241 B2 | 1/2011 | Brock et al. |
| 8,052,597 B2 | 11/2011 | Boulais |
| 8,100,031 B2 | 1/2012 | Zubiate et al. |
| 8,192,422 B2 | 6/2012 | Zubiate et al. |
| 8,656,697 B2 | 2/2014 | Zubiate et al. |
| 9,370,342 B2 * | 6/2016 | Zubiate .................. A61B 1/008 |
| 2002/0087048 A1 | 7/2002 | Brock et al. |
| 2002/0087148 A1 | 7/2002 | Brock et al. |
| 2002/0087166 A1 | 7/2002 | Brock et al. |
| 2002/0107509 A1 | 8/2002 | Neuberger et al. |
| 2002/0108644 A1 | 8/2002 | Hoadley et al. |
| 2004/0143163 A1 | 7/2004 | Palmer et al. |
| 2005/0119527 A1 | 6/2005 | Banik et al. |

(56) References Cited

U.S. PATENT DOCUMENTS

| | | |
|---|---|---|
| 2005/0131279 A1 | 6/2005 | Boulais et al. |
| 2005/0197531 A1 | 9/2005 | Cabiri et al. |
| 2005/0240078 A1 | 10/2005 | Kwon et al. |
| 2005/0245789 A1 | 11/2005 | Smith et al. |
| 2005/0273084 A1 | 12/2005 | Hinman et al. |
| 2006/0052664 A1 | 3/2006 | Julian et al. |
| 2006/0058582 A1 | 3/2006 | Maahs et al. |
| 2006/0111209 A1 | 5/2006 | Hinman et al. |
| 2006/0161045 A1 | 7/2006 | Merril et al. |
| 2006/0178560 A1 | 8/2006 | Saadat et al. |
| 2007/0005088 A1 | 1/2007 | LeHuec et al. |
| 2007/0015965 A1 | 1/2007 | Cox et al. |
| 2007/0043259 A1 | 2/2007 | Jaffe et al. |
| 2007/0249999 A1 | 10/2007 | Sklar et al. |
| 2008/0039690 A1* | 2/2008 | Zubiate .............. A61B 1/00071 600/141 |
| 2008/0051631 A1 | 2/2008 | Dejima et al. |
| 2008/0065098 A1 | 3/2008 | Larkin |
| 2008/0091170 A1 | 4/2008 | Vargas et al. |
| 2008/0097471 A1 | 4/2008 | Adams et al. |
| 2008/0125794 A1 | 5/2008 | Brock et al. |
| 2008/0132913 A1 | 6/2008 | Brock et al. |
| 2008/0177285 A1 | 7/2008 | Brock et al. |
| 2008/0205980 A1 | 8/2008 | Zubiate et al. |
| 2008/0287963 A1 | 11/2008 | Rogers et al. |
| 2009/0069842 A1 | 3/2009 | Lee et al. |
| 2009/0171147 A1 | 7/2009 | Lee et al. |
| 2009/0171151 A1 | 7/2009 | Choset et al. |
| 2009/0216245 A1 | 8/2009 | Viola |
| 2009/0264759 A1 | 10/2009 | Byrd |
| 2010/0076451 A1 | 3/2010 | Zwolinski et al. |
| 2010/0121141 A1 | 5/2010 | Rontal |
| 2010/0249759 A1 | 9/2010 | Hinman et al. |
| 2011/0022078 A1 | 1/2011 | Hinman |
| 2011/0313243 A1* | 12/2011 | Zubiate .................. A61B 1/008 600/104 |

FOREIGN PATENT DOCUMENTS

| | | |
|---|---|---|
| EP | 1884185 A1 | 2/2008 |
| EP | 1927312 A1 | 6/2008 |
| JP | S6048294 A | 3/1985 |
| JP | 60-84524 | 5/1985 |
| WO | WO-9405200 A1 | 3/1994 |
| WO | WO-9501751 A1 | 1/1995 |
| WO | WO-2003073920 A2 | 9/2003 |
| WO | WO-2003092476 A2 | 11/2003 |
| WO | WO-2006083306 A2 | 8/2006 |

OTHER PUBLICATIONS

Brown et al., "Design and Control of a Second-Generation Hyper-Redundant Mechanism," International Conference of Robots and Systems, San Diego, CA, Oct. 29-Nov. 2, 2007.

Wolf et al., "A Mobile Hyper Redundant Mechanism for Search and Rescue Tasks," International Conference on Robots and Systems, Las Vegas, NV, Oct. 2003.

\* cited by examiner

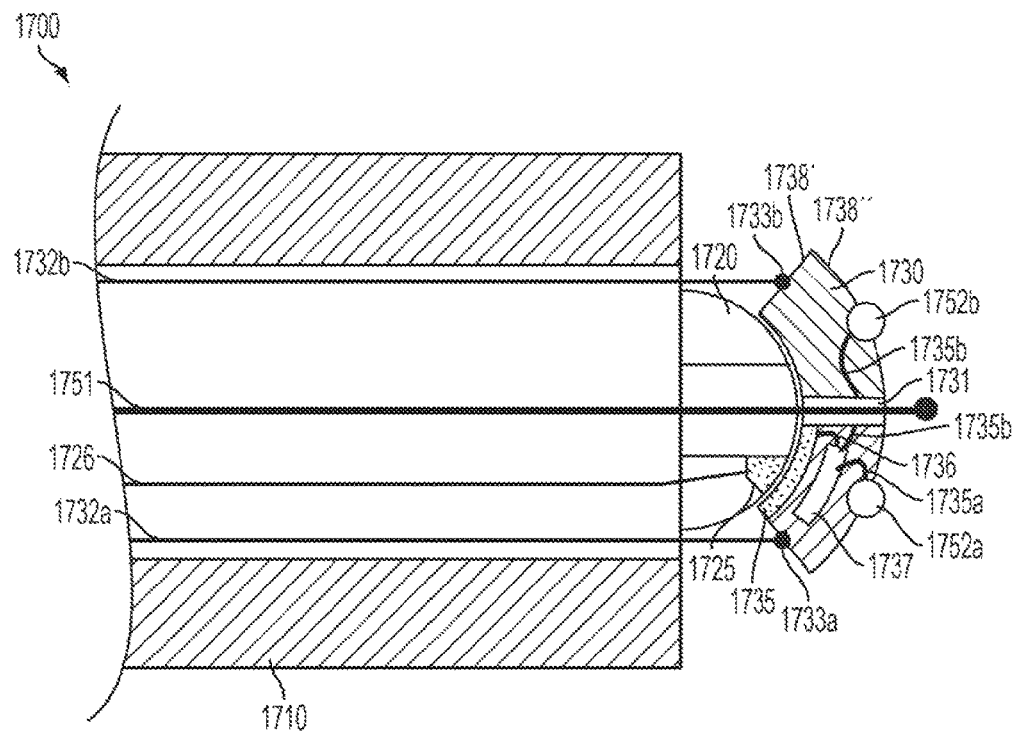
FIG. 17
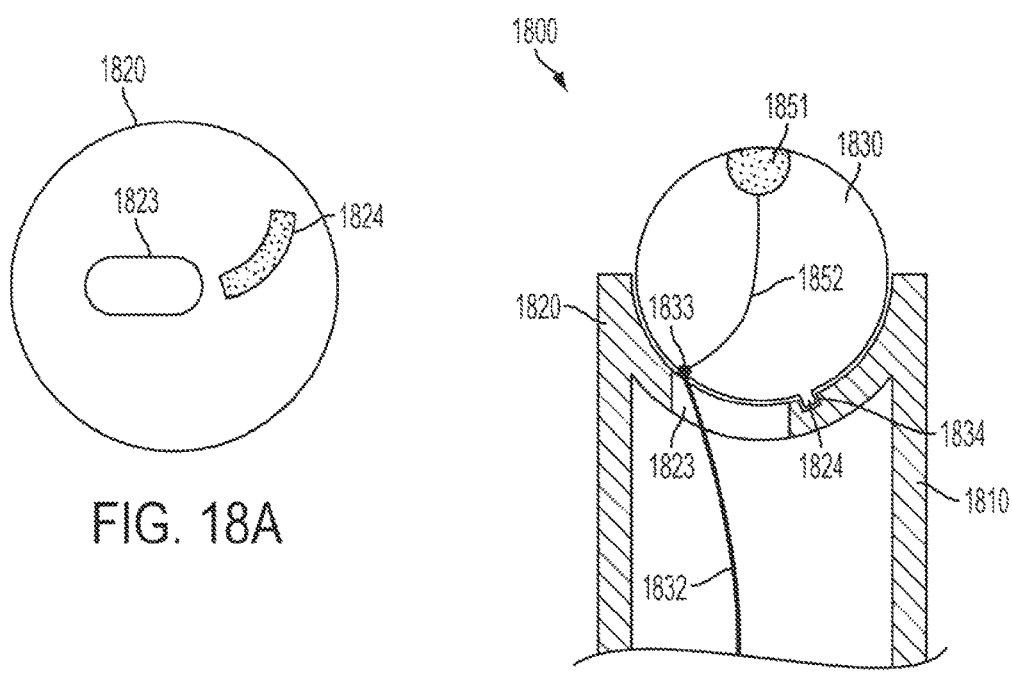
FIG. 18A
FIG. 18B

MULTI-LINKED ENDOSCOPIC DEVICE WITH SPHERICAL DISTAL ASSEMBLY

CROSS REFERENCE TO RELATED APPLICATIONS

This application is a continuation of and claims the benefit of U.S. patent application Ser. No. 13/062,659, filed Apr. 11, 2011, issued as U.S. Pat. No. 9,370,342, which a national stage application of PCT/US09/56238, filed Sep. 8, 2009, which claims the benefit of the filing date of Provisional Patent Application No. 61/094,606 filed Sep. 5, 2008, the disclosures of which are hereby incorporated by reference in their entireties. This application is related to U.S. patent application Ser. No. 11/630,279, filed Dec. 20, 2006 issued as U.S. Pat. No. 9,011,318; U.S. patent application Ser. No. 11/838,519, filed Aug. 14, 2007, issued as U.S. Pat. No. 8,192,422, U.S. patent application Ser. No. 11/876,304, filed Oct. 22, 2007, issued as U.S. Pat. No. 7,946,546; U.S. patent application Ser. No. 11/923,246, filed Oct. 24, 2007, issued as U.S. Pat. No. 7,854,109; U.S. patent application Ser. No. 12/038,560, filed Feb. 27, 2008, issued as U.S. Pat. No. 8,100,031; U.S. patent application Ser. No. 12/038,691, filed Feb. 27, 2008, issued as U.S. Pat. No. 8,459,138; U.S. patent application Ser. No. 12/038,729, filed Feb. 27, 2008 and PCT/US09/40548, filed Apr. 14, 2009.

BACKGROUND

This application discloses an invention that is related, generally and in various embodiments, to a multi-linked or continuum device, and other devices having, a rotatable distal assembly. Typically, most medical probes and/or multi-linked devices can only "see forward", that is, the orientation of the leading, or distal end, is parallel to the direction of movement of the probe or multi-linked device. In order to look or aim in any non-moving direction, the probe or device must bend or flex in the desired viewing direction, which occupies volume. In certain applications, the volume required for bending the probe to view other directions is limited, or in extreme situations, non-existent.

SUMMARY

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, a device for performing a procedure may include an elongate tube having a proximal end and a distal end and an adapted link having a proximal end and a distal end. The distal end may include a first mating surface, where the proximal end may be configured to attach to the distal end of the elongate tube. The device may also include a rotating link having a second mating surface configured to rotatably interface with the adapted link first mating surface.

In an embodiment, a method of performing a procedure may include selecting a device and rotating a rotating link of the device.

In an embodiment, a steerable multi-linked device may include a first link and a plurality of intermediate links. A first one of the intermediate links may be movably coupled to the first link. The device may also include an adapted link movably coupled to one of the intermediate links at a first end and having a concave surface at the second end and a spherical link fitted in said concave surface of said adapted link.

In an embodiment, a steerable multi-linked device may include a first multi-linked mechanism and a second multi-linked mechanism. The second multi-linked mechanism may include a first link, a plurality of intermediate links, an adapted link, movably coupled to one of the intermediate links at a first end and having a concave surface at the second end and a spherical link fitted in the concave surface of the adapted link. A first one of the intermediate links may be movably coupled to the first link.

BRIEF DESCRIPTION OF DRAWINGS

Various embodiments of the invention are described herein by way of example in conjunction with the following figures.

FIGS. 3A-13D illustrates various embodiments of individual links of the steerable multi-linked device of FIG. 12.

FIG. 17 illustrates various embodiments of a device including a rotatable distal assembly comprising a spherical adapted link and a cup shaped rotatable link.

FIG. 18A illustrates various embodiments of a cup assembly including a curvilinear groove.

FIG. 18B illustrates various embodiments of a device including a rotatable distal assembly comprising the cup assembly of FIG. 18A and a mating rotating sphere.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the invention described herein may be utilized to control movement of a multi-linked device such as the steerable multi-linked device described herein. For ease of explanation purposes, the invention will be described in the context of its use with various embodiments of the steerable multi-linked device described herein. However, one skilled in the art will appreciate that the invention may be utilized with other types of multi-linked devices.

Figure 1A:
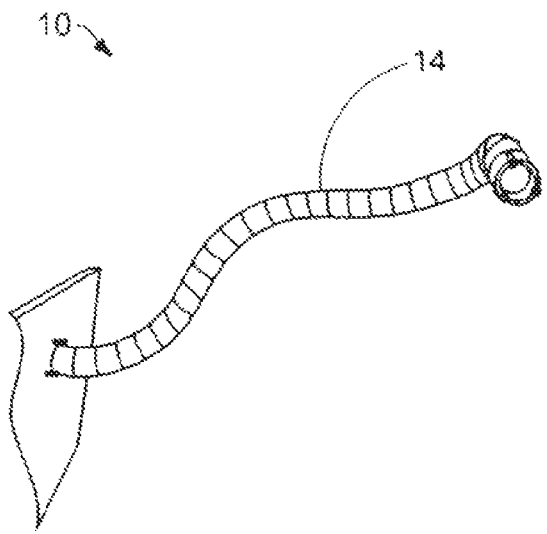
FIGS. 1A and 1B illustrate various embodiments of a steerable multi-linked device.
Figure 1B:
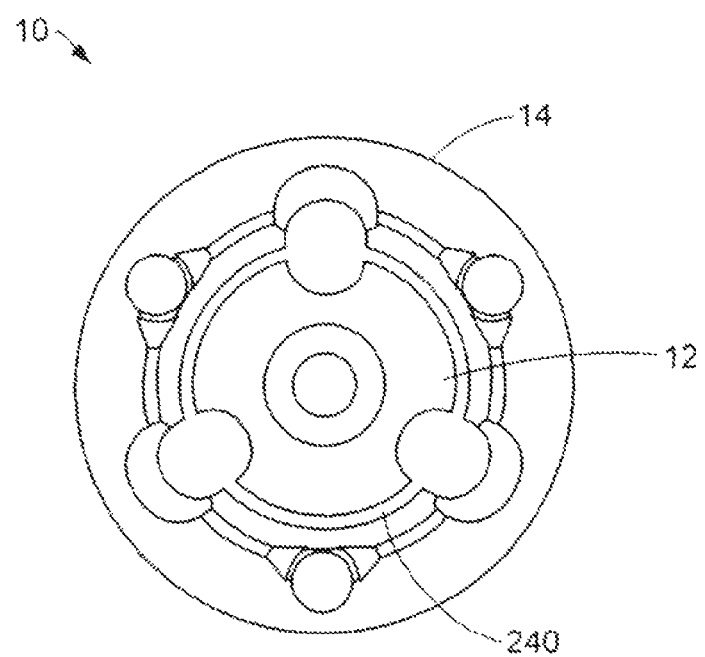

FIGS. 1A and 1B illustrate various embodiments of a steerable multi-linked device 19. According to various embodiments, the steerable multi-linked device may be a snake robot, a continuum robot or the like. Various embodiments of the device 10 may be utilized for medical procedures (e.g., as a robotic bore, positioning device, ablation tool, camera or instrument support, or guidance system for minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

The device 10 comprises a first mechanism 12 and a second mechanism 14. According to various embodiments, a mechanism may be a snake robot, a continuum robot or the like. According to various embodiments, the second mechanism 14 is structured and arranged to receive and surround the first mechanism 12 as shown in FIG. 1B. Thus, the first mechanism and second mechanism may be concentric. For such embodiments, the first mechanism 12 may be considered the inner mechanism or the core mechanism, and the second mechanism 14 may be considered the outer mechanism or the sleeve mechanism. According to other embodiments, the first and second mechanisms 12, 14 may be structured and arranged to have a relationship other than a concentric relationship. For example, one skilled in the art will appreciate that, according to various embodiments, the first and second mechanisms 12, 14 may be structured and arranged to operate in a side-by-side arrangement, where the first mechanism 12 operates adjacent to the second mechanism 14. According to various embodiments, additional and/or alternate configurations may be used within the scope of this disclosure. According to various embodiments, a three-dimensional space 240 may be provided between the first and second mechanisms. This space will be described in more detail below.

As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. Both the first mechanism 12 and the second mechanism 14 may be steerable mechanisms. Accordingly, it will be appreciated that the device 10 may be utilized to navigate a luminal space as well as any three-dimensional path within an intracavity space. According to various embodiments, the device 10 may advance by alternating the operation of the first mechanism 12 and the second mechanism 14 between a limp mode and a rigid mode.

According to various embodiments, the device 10 may also comprise one or more cables. According to various embodiments, one or more of the cables may be steering cables and/or tensioning cables. For example, the device may include three steering cables and one tensioning cable.

Figure 2:
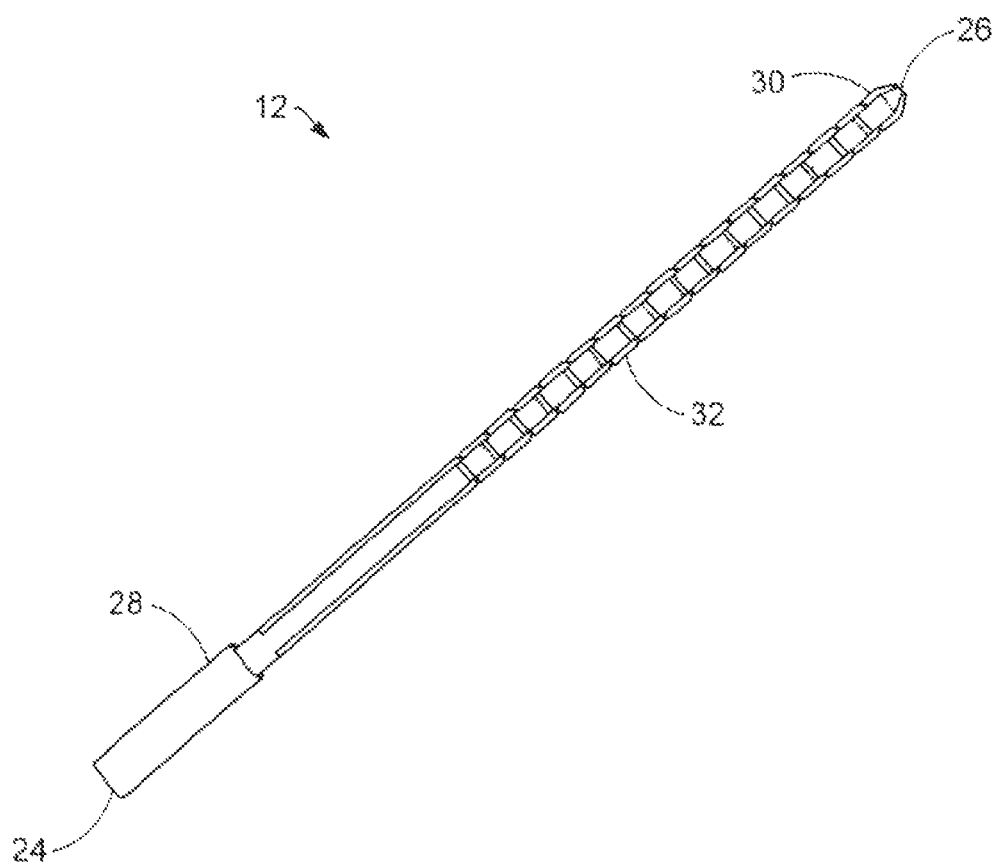
FIG. 2 illustrates various embodiments of a core mechanism of the device of FIG. 1.

FIG. 2 illustrates various embodiments of the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 may comprise a first link 28, a second link 30, and one or more intermediate links 32 between the first and second links 28, 30. The first link 28 may be considered the proximal link, and the second link 30 may be considered the distal link.

Figure 3A:
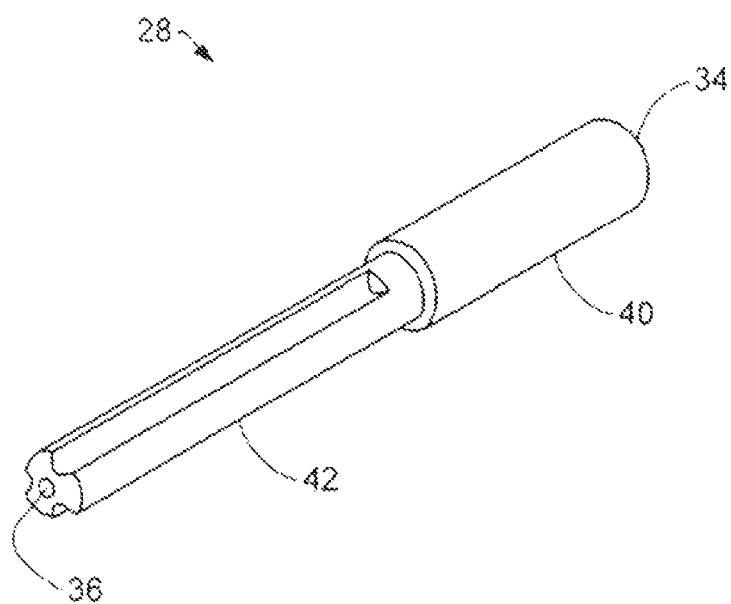
FIGS. 3A-3C illustrate various embodiments of a proximal Fmk of the core mechanism.
Figure 3B:
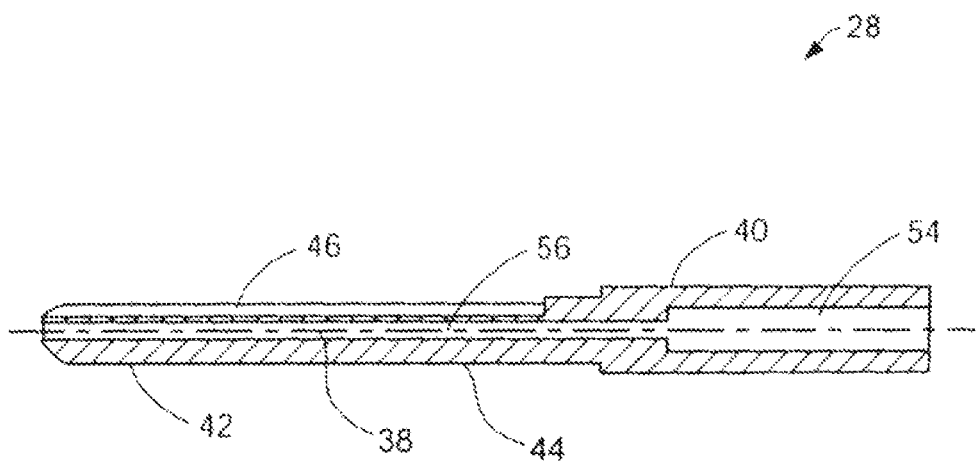
Figure 3C:
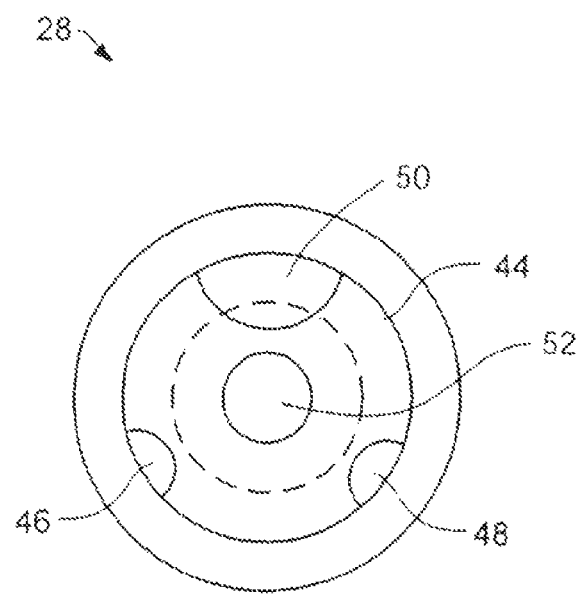

FIGS. 3A-3C illustrate various embodiments of the first link 28 (inner proximal link) of the first mechanism 12. The first link 28 includes a first end 34 and a second end 36, and defines a longitudinal axis 38 that passes through the center of the first end 34 and the center of the second end 36 as shown in FIG. 3B. The first link 28 may be fabricated from any suitable material. According to various embodiments, the first link 28 is fabricated from a fiber reinforced material such as, for example, G10/F4 Garolite®. The first link 28 has a generally cylindrical shaped exterior and is described in more detail hereinbelow.

The first link 28 comprises a first portion 40 and a second portion 42. The first portion 40 may be considered the proximal portion and the second portion 42 may be considered the distal portion. The first portion 40 may be fabricated integral with the second portion 42. The first portion 40 has a cylindrical shaped exterior, and extends from the first end 34 of the first link 28 toward the second end 36 of the first link 28. According to various embodiments, the diameter of the first portion 40 may be on the order of approximately 6.35 millimeters. Other sizes are possible.

The second portion 42 has a generally cylindrical shaped exterior, with other features described below. The second portion 42 has a cylindrical shaped exterior where it contacts the first portion 40, and tapers toward the second end 36 of the first link 28. The second portion 42 may be shaped in the form of a generally segmented hemisphere at the second end 36 of the first link 28. According to various embodiments, the diameter of the second portion 42 may be on the order of approximately 4.75 millimeters where it contacts the first portion 40. Other sizes are possible.

The second portion 42 comprises a first surface 44. The first surface 44 may be considered the outer surface of the second portion 42. The second portion 42 defines a first groove 46 parallel to the longitudinal axis 38 along the first surface 44, a second groove 48 parallel to the longitudinal axis 38 along the first surface 44, and a third groove 50 parallel to the longitudinal axis 38 along the first surface 44. Each of the first, second and third grooves 46, 48, 50 extend along the first surface 44 toward the second end 36 of the first link 28. The first, second and third grooves 46, 48, 50 may be semi-tubular shaped and may be evenly spaced about the first surface 44 of the second portion 42 of the first link 28 as shown in FIG. 3C. According to various embodiments, the first, second, and third grooves 46, 48, 50 may be configured in the shape of a segmented cylinder. The size of each of the grooves 46, 48, 50 may be identical to one another or may be different from one another. For example, according to various embodiments, the first and second grooves 46, 48 may be configured as segments of a cylinder having a diameter on the order of approximately 1.25 millimeters, and the third groove 50 may be configured as a segment of a cylinder having a diameter on the order of approximately 2.50 millimeters. The length of the first link 28 may be on the order of approximately 65 millimeters. However, one skilled in the art will appreciate that the length or diameter of the first link 28 can vary based on the application.

The first link 28 also defines a passage 52 extending from the first end 34 to the second end 36 along the longitudinal axis 38 as shown in FIG. 3B. The passage 52 is of a size sufficient to allow at least one cable to pass therethrough. According to various embodiments, the passage 52 may be of a sufficient size to allow a tensioning cable to pass therethrough. According to various embodiments, the passage 52 is generally configured as a complex shape that comprises a combination of a first cylinder 54 that extends from the first end 34 toward the second end 36, and a second cylinder 56 that extends from the first cylinder 54 toward the second end 36. The diameter of the first cylinder 54 is larger than the diameter of the second cylinder 56. For example, according to various embodiments, the first cylinder 54 may have a diameter on the order of approximately 3.20 millimeters and the second cylinder 56 may have a diameter on the order of approximately 1.50 millimeters. Other sizes are possible.

Figure 4A:
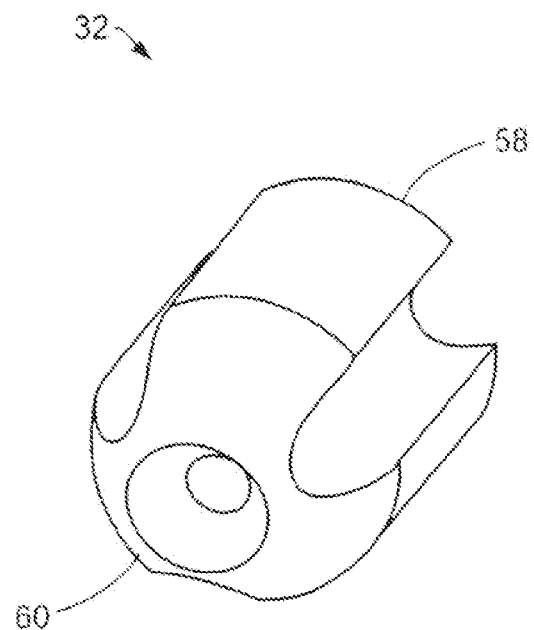
FIGS. 4A-4C illustrate various embodiments of an intermediate link of the core mechanism.
Figure 4B:
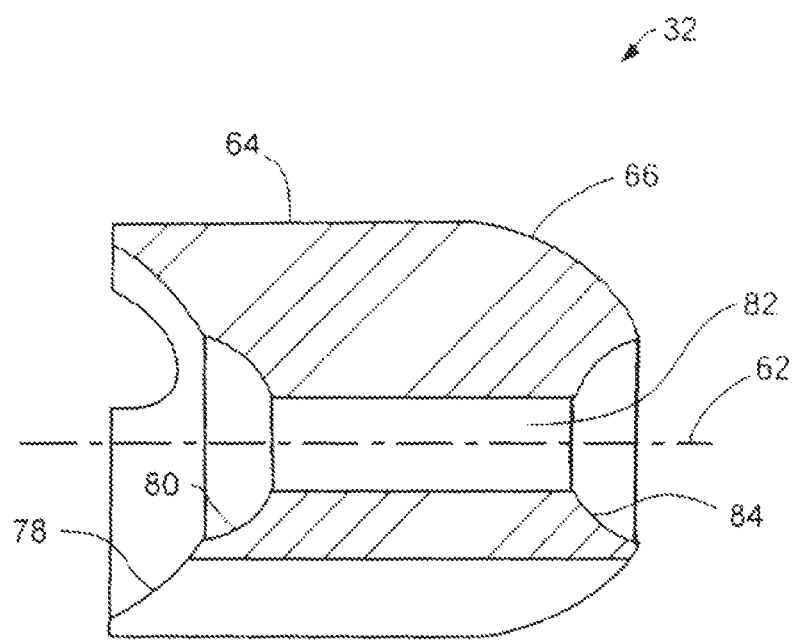
Figure 4C:
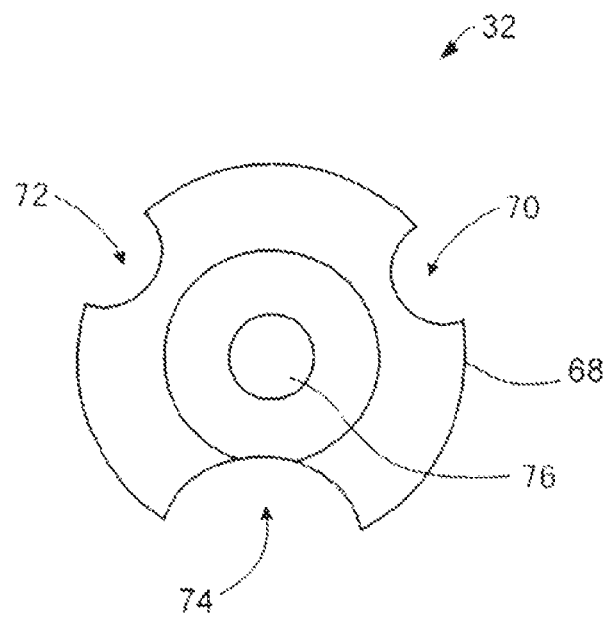

FIGS. 4A-4C illustrate various embodiments of one of the intermediate, links 32 (inner intermediate link) of the first mechanism 12. The intermediate link 32 is representative of the other intermediate links 32. The intermediate link 32 includes a first end 58 and a second end 60, and defines a longitudinal axis 62 that passes through the center of the first end 58 and the center of the second end 60 as shown in FIG. 4B. The intermediate link 32 may be fabricated, from any suitable material. According to various embodiments, the intermediate link 32 is fabricated from a fiber reinforced material such as, for example, G10/FR4 Garolite®. The intermediate link 32 has a generally bullet-shaped exterior and is described in more detail hereinbelow.

The intermediate link 32 comprises a first portion 64 and a second portion 66. The first portion 64 may be considered the proximal portion and the second portion 66 may be considered the distal portion. The first portion 64 may be fabricated integral with the second portion 66. The first portion 64 has a generally cylindrical shaped exterior, and extends from the first end 58 of the intermediate link 32 toward the second end 60 of the intermediate link 32. According to various embodiments, the second portion 66 has a generally cylindrical shaped exterior where it contacts the first portion 64, and tapers toward the second end 60 of the intermediate link 32. The exterior of the second portion 66 is configured in the form of a generally segmented hemisphere. According to various embodiments, the diameter of the intermediate link 32 may be on the order of approximately 4.75 millimeters at the first end 58 thereof. The length of the intermediate link 32 may be on the order of approximately 5.85 millimeters. However, one skilled in the art will appreciate that the length or diameter of the intermediate link 32 can vary based on the application.

The intermediate link 32 also comprises a first surface 68 that extends from the first end 58 of the intermediate link 32 to the second end 60 of the intermediate link 32. The first surface 68 may be considered the outer surface of the intermediate link 32. The intermediate link 32 also defines a first groove 70 parallel to the longitudinal axis 62 along the first surface 68, a second groove 72 parallel to the longitudinal axis 62 along the first surface 68, and a third groove 74 parallel to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be evenly spaced about the first surface 68 of the intermediate link 32 as shown in FIG. 4C. According to various embodiments, the first, second, and third grooves 70, 72, 74 may be configured in the shape of a segmented cylinder. The size of each of the grooves 70, 72, 74 may be identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to receive and partially surround any of a variety of tools or instruments (e.g., ablation tools) which may pass from the first end 24 of the multi-linked device 10 to the second end 26 of the multi-linked device 10.

The intermediate link 32 also defines a passage 76 extending from the first end 58 to the second end 60 along the longitudinal axis 62 as shown in FIG. 4B. The passage 76 may be of a size sufficient to allow one or more cables to pass therethrough. According to various embodiments, the passage 76 may be of a size sufficient to allow a tensioning cable to pass therethrough. According to various embodiments, the passage 76 is generally configured as a complex shape that comprises a combination of a first segmented hemisphere 78 that extends from the first end 58 toward the second end 60, a second segmented hemisphere 80 that extends from the first segmented hemisphere 78 toward the second end 60, a cylinder 82 that extends from the second segmented hemisphere 80 toward the second end 60, and a third segmented hemisphere 84 that extends from the cylinder 82 to the second end 60 of the intermediate link 32. According to various embodiments, the first segmented hemisphere 78 represents a portion of a sphere having a diameter on the order of approximately 4.75 millimeters, the second segmented hemisphere 80 represents a portion of a sphere having a diameter on the order of approximately 2.25 millimeters, the cylinder 82 may have a diameter on the order of approximately 1.0 millimeter, and the third segmented hemisphere 84 represents a portion of a sphere having a diameter on the order of approximately 2.25 millimeters. Other sizes are possible.

The first segmented hemisphere 78 of the passage 76 is configured to receive the second end 36 of the first link 28 when the first link 28 is coupled to the intermediate link 32. Similarly, for a given intermediate link 32, the first segmented hemisphere 78 of the passage 76 is configured to receive the second end 60 of another intermediate link 32 when the other intermediate link 32 is coupled to the given intermediate link 32. The third segmented hemisphere 84 may serve to reduce the pinching or binding a cable when one intermediate link 32 moves relative to an adjacent intermediate link 32 coupled thereto. Similarly, when the second link 30 is coupled to a given intermediate link 32, the third segmented hemisphere 84 may serve to reduce the pinching or binding of a cable when the second link 30 moves relative to the given intermediate link 32.

With the above described structure, the first link 28 may be coupled to the intermediate link 32 by seating the second end 36 of the first link 28 in the first segmented hemisphere 78 of the passage 76 of the intermediate link 32. As the convex configuration of the second end 36 of the first link 28 generally corresponds with the concave configuration of the first segmented hemisphere 78 of the passage 76 of the intermediate link 32, the first link 28 may be coupled to the intermediate link 32 such that the longitudinal axis 38 and the first, second and third grooves 46, 48, 50 of the first link 28 are respectively aligned with the longitudinal axis 62 and the first, second and third grooves 70, 72, 74 of the intermediate link 32. The intermediate link 32 may be moved relative to the first link 28 such that the longitudinal axis 62 of the intermediate link 32 is not aligned with the longitudinal axis 38 of the first link 28. According to various embodiments, the configuration of the first link 28 and the intermediate link 32 allows for the intermediate link 32 to be moved relative to the first link 28 coupled thereto such that the longitudinal axis 38 of the first link 28 and the longitudinal axis 62 of the intermediate link 32 are up to approximately 25° out of alignment with one another. Similarly, one intermediate link 32 may be coupled to another intermediate link 32, and so on, by seating the second end 60 of one intermediate link 32 in the first segmented hemisphere 78 of the passage 76 of another intermediate link 32. As the convex configuration of the second end 60 of the intermediate link 32 generally corresponds with the concave configuration of the first segmented hemisphere 78 of the passage 76 of the intermediate link 32, the intermediate links 32 may be coupled such that the respective longitudinal axes 62 and the respective first, second and third grooves 46, 48, 50 of the intermediate links 32 are aligned. The coupled intermediate links 32 may be moved relative to one another such that the respective longitudinal axes 62 of the coupled intermediate links 32 are not aligned. According to various embodiments, the configuration of the coupled intermediate links 32 allows for one intermediate link 32 to be moved relative to an adjacent intermediate link 32 coupled thereto such that the respective longitudinal axes 62 are up to approximately 25° out of alignment with one another.

Figure 5A:
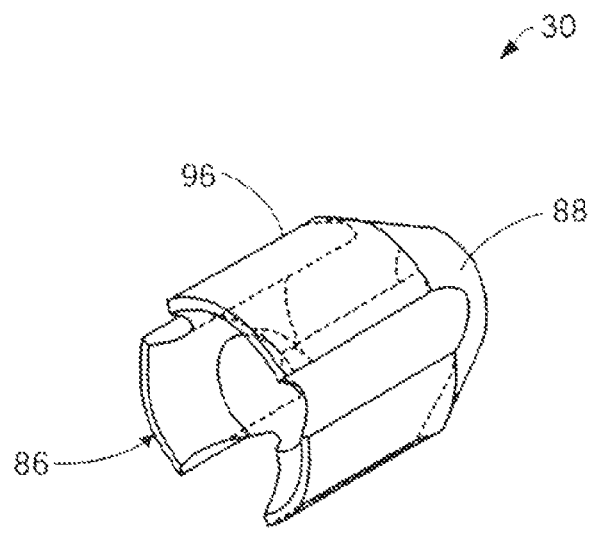
FIGS. 5A-5C illustrate various embodiments of a distal link of the core mechanism.
Figure 5B:
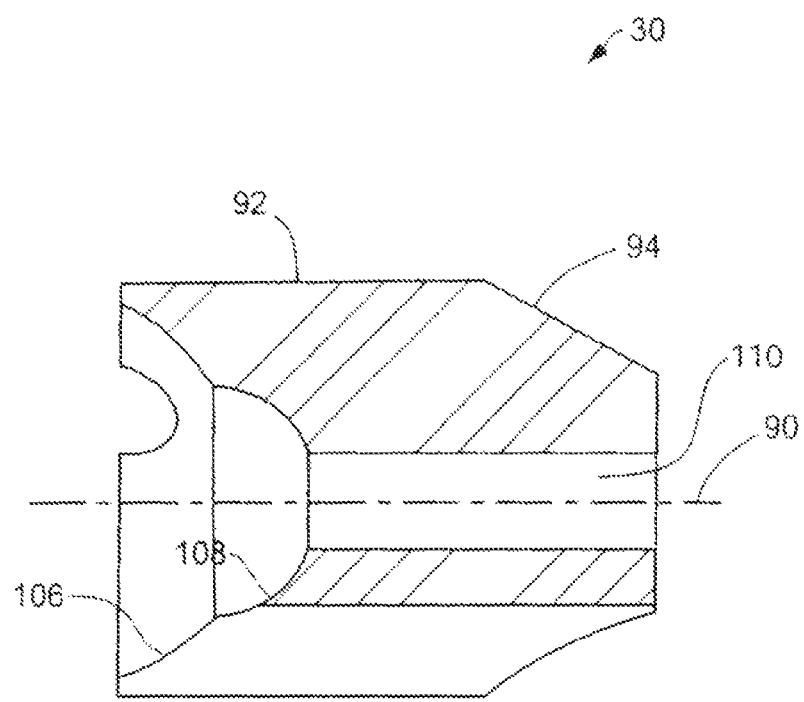
Figure 5C:
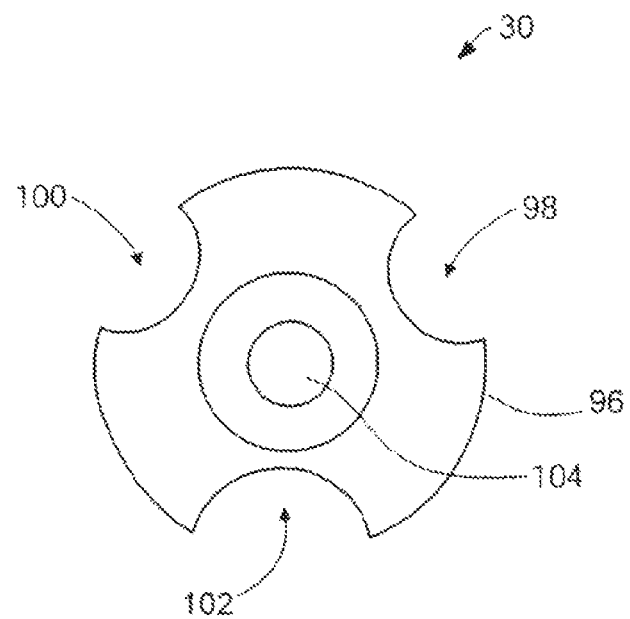

FIGS. 5A-5C illustrate various embodiments of the second link 30 (inner distal link) of the first mechanism 12. The second link 30 includes a first end 86 and a second end 88, and defines a longitudinal axis 90 that passes through the center of the first end 86 and the center of the second end 88 as shown in FIG. 5B. The second link 30 may be fabricated from any suitable material. According to various embodiments, the second link 30 is fabricated from a thermoplastic material such as, for example, Delrin®.

The second link 30 comprises a first portion 92 and a second portion 94. The first portion 92 may be considered the proximal portion and the second portion 94 may be considered the distal portion. The first portion 92 may be fabricated integral with the second portion 94. The first portion 92 has a generally cylindrical shaped exterior, and extends from the first end 86 of the second link 30 toward the second end 88 of the second link 30. According to various embodiments, the second portion 94 has a generally cylindrical shaped exterior where it contacts the first portion 92, and tapers toward the second end 88 of the second link 30. The exterior of the second portion 94 is configured in the form of a generally segmented cone. According to various embodiments, the diameter of the second link 30 may be on the order of approximately 4.75 millimeters at the first end 86 thereof, and the taper of the second portion 94 may be at an angle of approximately 30° relative to the exterior of the first portion 92. The length of the second link 30 may be on the order of approximately 5.90 millimeters. However, one skilled in the art will appreciate that the length or diameter of the second link 30 can vary based on the application.

The second link 30 also comprises a first surface 96 that extends from the first end 86 of the second link 30 to the second end 88 of the second link 30. The first surface 96 may be considered the outer surface of the second link 30. The second link 30 also defines a first groove 98 parallel to the longitudinal axis 90 along the first surface 96, a second groove 100 parallel to the longitudinal axis 90 along the first surface 96, and a third groove 102 parallel to the longitudinal axis 90 along the first surface 96. Each of the first, second and third grooves 98, 100, 102 extend along the first surface 96 from the first end 86 of the second link 30 toward the second end 88 of the second link 30. The first, second and third grooves 98, 100, 102 may be semi-tubular shaped and may be evenly spaced about the first surface 96 of the second link 30 as shown in FIG. 5C. According to various embodiments, the first, second, and third grooves 98, 100, 102 may be configured in the shape of a segmented cylinder. The size of each of the grooves 98, 100, 102 may be identical to one another or may be different from one another. For example, according to various embodiments, the first and second grooves 98, 100 are configured as segments of a cylinder having a diameter on the order of approximately 1.25 millimeters at the first end 86 of the second link 30, and the third groove 102 is configured as a segment of a cylinder having a diameter on the order of approximately 2.50 millimeters at the first end 86 of the second link 30. The first, second and third grooves 98, 100, 102 are each configured to receive and partially surround any of a variety of tools or instruments (e.g., ablation tools) which may pass from the first end 24 of the multi-linked device 10 to the second end 26 of the multi-linked device 10.

The second link 30 also defines a passage 104 extending from the first end 86 to the second end 88 along the longitudinal axis 90 as shown in FIG. 5B. The passage 104 may be of a size sufficient to allow at least one cable to pass therethrough. According to various embodiments, the passage 104 may be of a size sufficient to allow a tensioning cable to pass therethrough. According to various embodiments, the passage 104 is generally configured as a complex shape that comprises a combination of a first segmented hemisphere 106 that extends from the first end 86 toward the second end 88, a second segmented hemisphere 108 that extends from the first segmented hemisphere 106 toward the second end 88, and a cylinder 110 that extends from the second segmented hemisphere 108 to the second end 88 of the second link 30. According to various embodiments, the first segmented hemisphere 106 represents a portion of a sphere having a diameter on the order of approximately 4.75 millimeters, the second segmented hemisphere 108 represents a portion of a sphere having a diameter on the order of approximately 2.50 millimeters, and the cylinder 110 may have a diameter on the order of approximately 1.0 millimeter. The first segmented hemisphere 106 of the passage 104 may be configured to receive the second end 60 of an intermediate link 32 when the intermediate link 32 is coupled to the second link 30.

With the above described structure, an intermediate link 32 may be coupled to the second link 30 by seating the second end 60 of the intermediate link 32 in the first segmented hemisphere 106 of the passage 104 of the second link 30. As the convex configuration of the second end 60 of the intermediate link 32 generally corresponds with the concave configuration of the first segmented hemisphere 106 of the passage 104 of the second link 30, the intermediate link 32 may be coupled to the second link 30 such that the longitudinal axis 62 and the first, second and third grooves 70, 72, 74 of the intermediate link 32 are respectively aligned with the longitudinal axis 90 and the first, second and third grooves 98, 100, 102 of the second link 30. The second link 30 may be moved relative to intermediate link 32 coupled thereto such that the respective longitudinal axes 62, 90 are not aligned. According to various embodiments, the configuration of the second link 30 allows for an intermediate link 32 coupled thereto to be moved relative to the second link 30 such that the respective longitudinal axes 62, 90 are up to approximately 25° out of alignment with one another.

Figure 6:
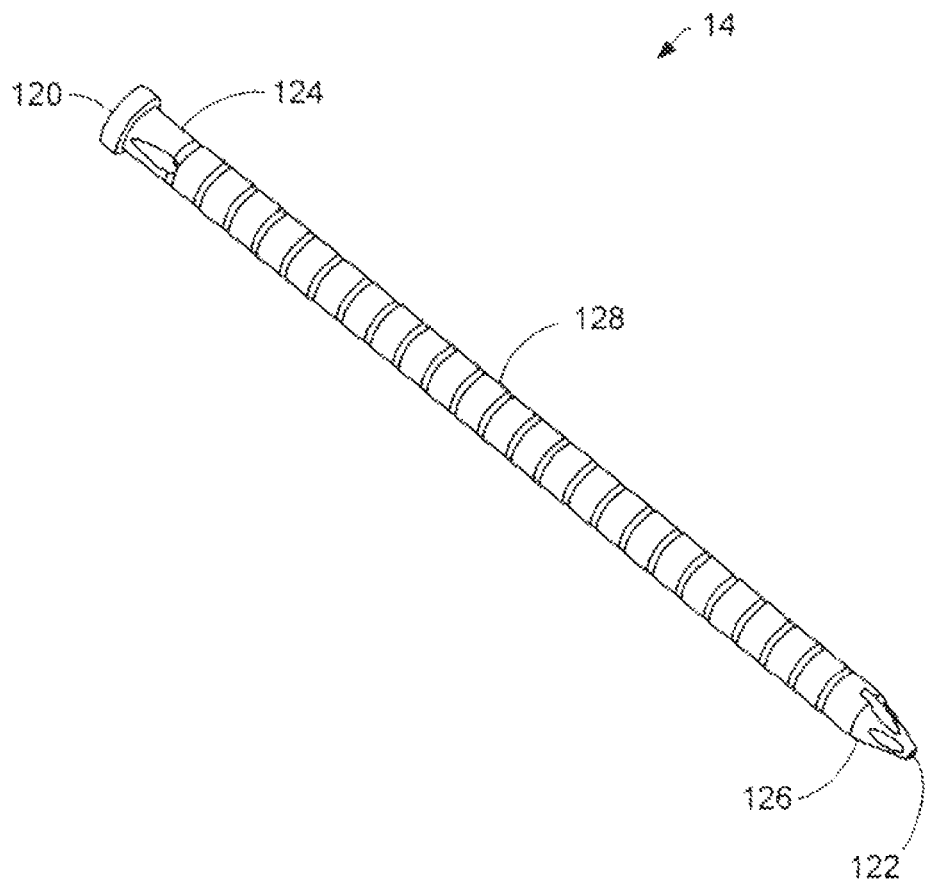
FIG. 6 illustrates various embodiments of a sleeve mechanism of the device of FIG. 1.

FIG. 6 illustrates various embodiments of the second mechanism 14 of the device 10. The second mechanism 14 is a multi-linked mechanism and includes a first end 120 and a second end 122. The first end 120 may be considered the proximal end and the second end 122 may be considered the distal end. The second mechanism 14 comprises a first link 124, a second link 126, and any number of intermediate links 128 between the first and second links 124, 126. The first link 124 may be considered the proximal link, and the second link 126 may be considered the distal link.

Figure 7A:
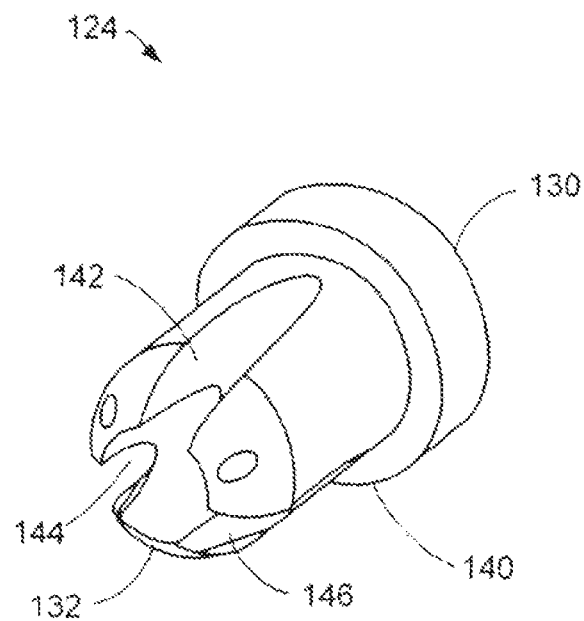
FIGS. 7A-7C illustrate various embodiments of a proximal link of the sleeve mechanism.
Figure 7B:
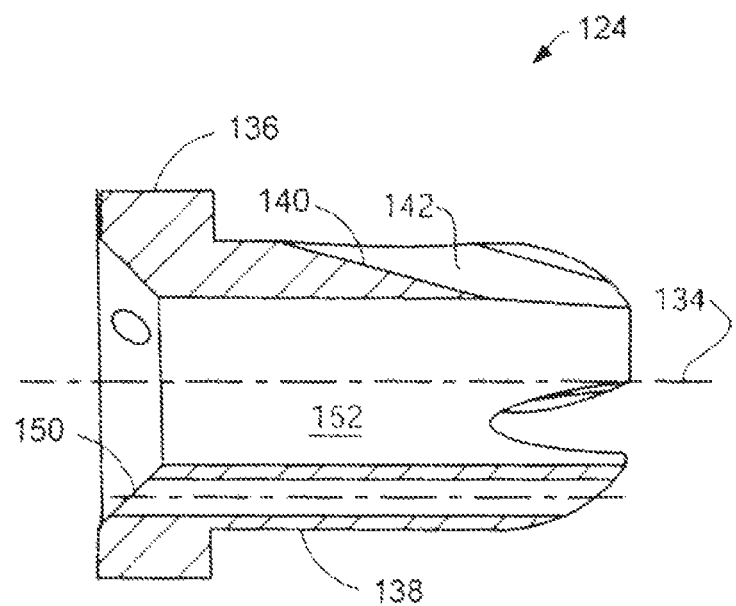
Figure 7C:
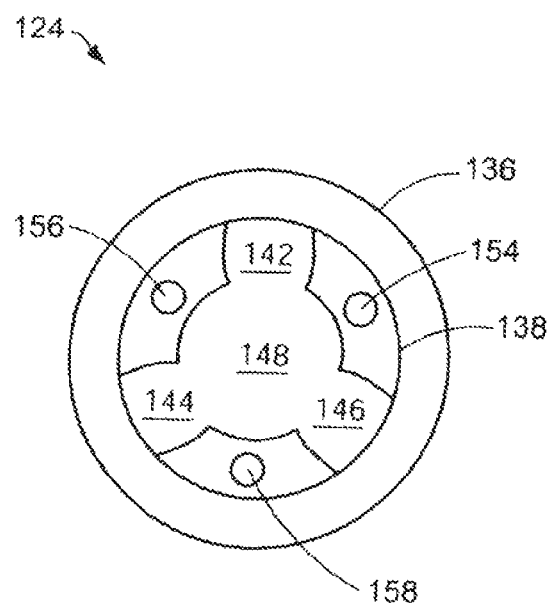

FIGS. 7A-7C illustrate various embodiments of the first link 124 (outer proximal link) of the second mechanism 14. The first link 124 includes a first end 130 and a second end 132, and defines a longitudinal axis 134 that passes through the center of the first end 130 and the center of the second end 132 as shown in FIG. 7B. The first link 124 may be fabricated from any suitable material. According to various embodiments, the first link 124 is fabricated from a stainless steel material such as, for example, 316 stainless steel. The first link 124 has a generally bullet-shaped exterior and is described in more detail hereinbelow.

The first link 124 comprises a first portion 136 and a second portion 138. The first portion 136 may be considered the proximal portion and the second portion 138 may be considered the distal portion. The first portion 136 may be fabricated integral with the second portion 138. The first portion 136 has a cylindrical shaped exterior, and extends from the first end 130 of the first link 124 toward the second end 132 of the first link 124. According to various embodiments, the diameter of the first portion 136 may be on the order of approximately 12.70 millimeters. Other sizes are possible.

The second portion 138 has a generally cylindrical shaped exterior. The second portion 138 has a cylindrical shaped exterior where it contacts the first portion 136, and tapers toward the second end 132 of the first link 124. The second portion 138 may be shaped in the form of a generally segmented hemisphere at the second end 132 of the first link 124. According to various embodiments, the diameter of the second portion 138 may be on the order of approximately 9.50 millimeters where it contacts the first portion 136. Other sizes and shapes are possible.

The second portion 138 comprises a first surface 140. The first surface 140 may be considered the outer surface of the second portion 138. The second portion 138 defines a first groove 142 along the first surface 140, a second groove 144 along the first surface 140, and a third groove 146 along the first surface 140. Each of the first, second and third grooves 142, 144, 146 are oblique relative to the longitudinal axis 134 and extend along the first surface 140 toward the second end 132 of the first link 124. According to various embodiments, each of the grooves 142, 144, 146 are oriented at an angle on the order of approximately 15° relative to the longitudinal axis 134, As shown in FIG. 7C, the first, second and third grooves 142, 144, 146 may be evenly spaced about the first surface 140 of the first link 124. According to various embodiments, the first, second, and third grooves 142, 144, 146 may be configured in the shape of a segmented cylinder. The size of each of the grooves 142, 144, 146 may identical to one another or ma be different from one another. For example, according to various embodiments, each of the grooves 142, 144, 146 are configured as segments of respective cylinders having diameters on the order of approximately 3.0 millimeters. The first, second and third grooves 142, 144, 146 are each configured to facilitate the introduction of various tools or instruments (e.g., ablation tools) into the multi-linked device 10. The length of the first link 124 may be on the order of approximately 18.5 millimeters. However, one skilled in the art will appreciate that the length or diameter of the first link 124 can vary based on the application.

The first link 124 also defines a passage 148 extending from the first end 130 to the second end 132 along the longitudinal axis 134 as shown in FIG. 7B. The passage 148 is of a size sufficient to allow the first mechanism 12 to pass therethrough. According to various embodiments, the passage 148 is generally configured as a complex shape that comprises a combination of a segmented cone 150 that extends from the first end 130 toward the second end 132, and a cylinder 152 that extends from the segmented cone 150 to the second end 132 of the first link 124. According to various embodiments, the segmented cone 150 has a diameter on the order of approximately 7.0 millimeters at the first end 130 of the first link 124, and may be tapered at an angle on the order of approximately 45° relative to the longitudinal axis 134, The cylinder 152 may have a diameter on the order of approximately 5.50 millimeters. Other dimensions are possible.

The first link 124 also defines a first through-hole 154, a second through-hole 156, and a third through-hole 158. (See FIG. 7C). The first through-hole 154 is substantially parallel to the longitudinal axis 134, extends from the first portion 136 toward the second end 132, and is positioned between the passage 148 and the first surface 140. The second through-hole 156 is substantially parallel to the longitudinal axis 134, extends from the first portion 136 to the second end 132, and is positioned between the passage 148 and the first surface 140. The third through-hole 158 is substantially parallel to the longitudinal axis 134, extends from the first portion 136 to the second end 132, and is positioned between the passage 148 and the first surface 140. The first, second and third through-holes 154, 156, 158 are generally cylindrical shaped. According to various embodiments, the through-holes 154, 156, 158 are evenly spaced from one another as shown in FIG. 7C. The size of each of the through-holes 154, 156, 158 may be identical to one another or may be different from one another. For example, according to various embodiments, the respective diameters associated with the through-holes 154, 156, 158 may each be on the order of approximately 1.20 millimeters. The first through-hole 154 is configured to receive and surround a cable. The second through-hole 156 is configured to receive and surround a cable. The third through-hole 158 is configured to receive and surround a cable. The first, second and third through-holes 154, 156, 158 may serve as guidepaths for movement of the cables.

Figure 8A:
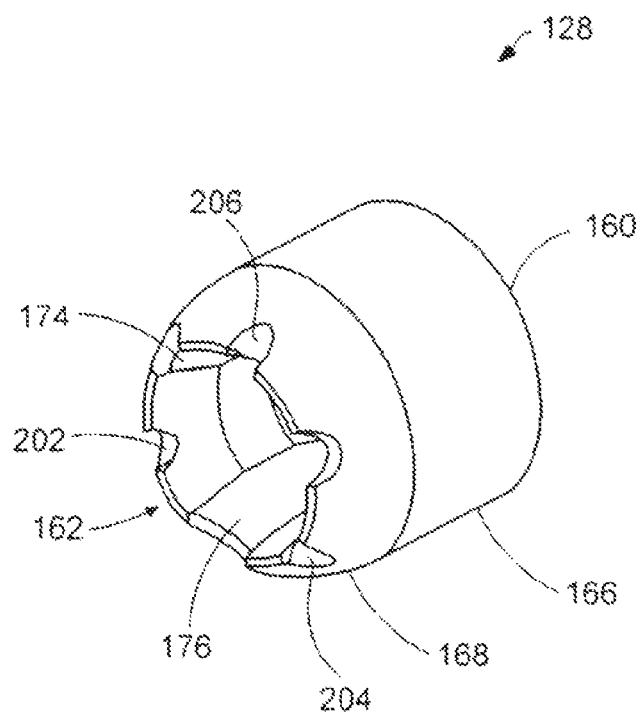
FIGS. 8A-8C illustrate various embodiments of an intermediate link of the sleeve mechanism.
Figure 8B:
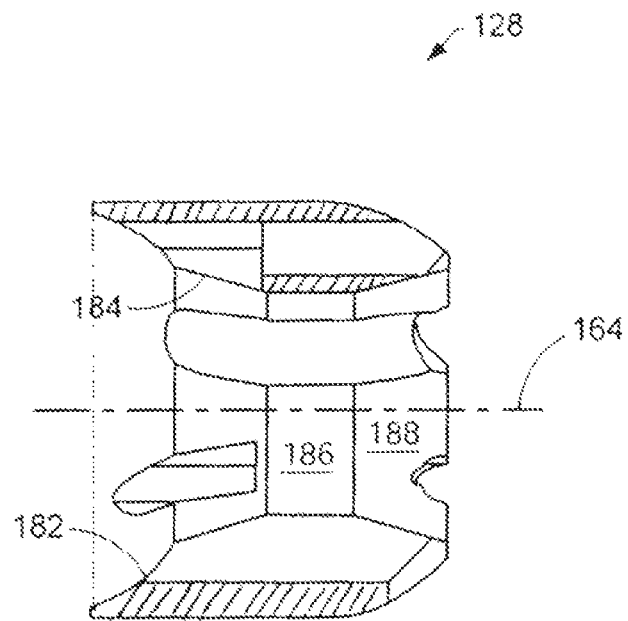
Figure 8C:
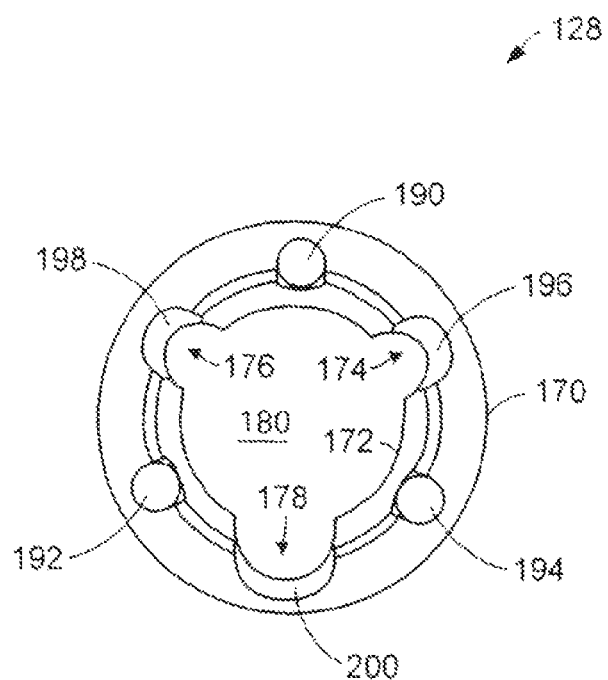

FIGS. 8A-8C illustrate various embodiments of one of the intermediate links 128 (outer intermediate link) of the second mechanism 14. The intermediate link 128 is representative of the other intermediate links 128. The intermediate link 128 includes a first end 160 and a second end 162, and defines a longitudinal axis 164 that passes through the center of the first end 160 and the center of the second end 162 as shown in FIG. 8B. The intermediate link 128 may be fabricated from any suitable material. According to various embodiments, the intermediate link 128 is fabricated from a polymer thermoplastic material such as, for example, polysulfone. The intermediate link 128 has a generally bullet-shaped exterior and is described in more detail hereinbelow.

The intermediate link 128 comprises to first portion 166 and a second portion 168. The first portion 166 may be considered the proximal portion and the second portion 168 may be considered the distal portion. The first portion 166 may be fabricated integral with the second portion 168. The first portion 166 has a generally cylindrical shape.

The intermediate link 128 also comprises a first surface 170 that extends from the first end 160 of the intermediate link 128 to the second end 162 of the intermediate link 128, and a second surface 170 that extends from the first end 160 of the intermediate link 128 to the second end 162 of the intermediate link 128. The first surface 170 may be considered the outer surface of the intermediate link 128, and the second surface 172 may be considered the inner surface of the intermediate link 128. The intermediate link 32 also defines a first groove 174 substantially parallel to the longitudinal axis 164 along the second surface 172, a second groove 176 substantially parallel to the longitudinal axis 164 along the second surface 172, and a third groove 178 substantially parallel to the longitudinal axis 164 along the second surface 172. Each of the first, second and third grooves 174, 176, 178 extend along the second surface 172 toward the second end 162 of the intermediate link 128. The first, second and third grooves 174, 176, 178 may be semi-tubular shaped and may be evenly spaced about the second surface 172 of the intermediate link 128 as shown in FIG. 8C. According to various embodiments, the first, second, and third grooves 174, 176, 178 may be configured in the shape of a segmented cylinder. The size of each of the grooves 174, 176, 178 may be identical to one another or may be different from one another. For example, according to various embodiments, the first and second grooves 174, 176 are configured as segments of cylinders having diameters on the order of approximately 1.75 millimeters at the first end 160 of the intermediate link 128, and the third groove 178 is configured as a segment of a cylinder having a diameter on the order of approximately 2.50 millimeters at the first end 160 of the intermediate link 128. The first, second and third grooves 174, 176, 178 are each configured to receive and partially surround any of a variety of tools or instruments (e.g., ablation tools) which may pass from the first end 24 of the multi-linked device 10 to the second end 26 of the multi-linked device 10.

The intermediate link 128 also defines a passage 180 extending from the first end 160 to the second end 162 along the longitudinal axis 164 as shown in FIG. 8B. The passage 180 is of as size sufficient to allow the first mechanism 12 to pass therethrough. According to various embodiments, the passage 180 is generally configured as a complex shape that comprises a combination of a segmented hemisphere 182 that extends from the first end 160 toward the second end 162, a first segmented cone 184 that extends from the segmented hemisphere 182 toward the second end 162, a cylinder 186 that extends from the first segmented cone 184 toward the second end 162, and a second segmented cone 188 that extends from the cylinder 186 to the second end 162 of the intermediate link 128. According to various embodiments, the segmented hemisphere 182 represents a portion of a sphere having a diameter on the order of approximately 9.65 millimeters, the first segmented cone 184 is tapered at an angle on the order of approximately 15° relative to the longitudinal axis 164, the cylinder 186 has a diameter on the order of approximately 5.50 millimeters, and the second segmented cone 188 is tapered at an angle on the order of approximately 15° relative to the longitudinal axis 164. The segmented hemisphere 182 of the passage 180 is configured to receive the second end 132 of the first link 124 when the first link 124 is coupled to the intermediate link 128. Similarly, for a given intermediate link 128, the segmented hemisphere 182 of the passage 180 is configured to receive the second end 162 of another intermediate link 128 when the other intermediate link 128 is coupled to the given intermediate link 128.

The intermediate link 128 also defines a first through-hole 190, a second through-hole 192, and a third through-hole 194. (See FIG. 8C). The first through-hole 190 is substantially parallel to the longitudinal axis 164, extends from the first portion 166 toward the second end 162, and is positioned between the passage 180 and the first surface 170. The second through-hole 192 is substantially parallel to the longitudinal axis 164, extends front the first portion 166 to the second end 162, and is positioned between the passage 180 and the first surface 170. The third through-hole 194 is substantially parallel to the longitudinal axis 164, extends from the first portion 166 to the second end 162, and is positioned between the passage 180 and the first surface 170. The first, second and third through-holes 190, 192, 194 are generally cylindrical shaped. According to various embodiments, the through-holes 190, 192, 194 are evenly spaced from one another. The size of each of the through-holes 190, 192, 194 may be identical to one another or may be different from one another. For example, according to various embodiments, the respective diameters associated with the through-holes 190, 192, 194 may each be on the order of approximately 1.25 millimeters. The first through-hole 190 is configured to receive and surround a cable. The second through-hole 192 is configured to receive and surround a cable. The third through-hole 194 is configured to receive and surround a cable. The first, second and third through-holes 190, 192, 194 may serve as guidepaths for movement of the cables.

As shown in FIG. 8C, the intermediate link 128 also defines first, second and third indents 196, 198, 200 at the second end 162 thereof resulting, in part, from the combination of the taper associated with the second portion 168 and the configuration and orientation of the first, second, and third grooves 174, 176, 178. The first, second and third indents 196, 198, 200 may be evenly spaced about the second end 162 of the intermediate link 128 as shown in FIG. 8C. The first, second and third indents 196, 198, 200 may serve to reduce the pinching, or binding of various tools or instruments (e.g., ablation tools) when one intermediate link 128 of the second mechanism 14 is moved relative to another intermediate ink 128 coupled thereto.

The intermediate link 128 also defines fourth, fifth and sixth indents 202, 204, 206 at the second end 162 thereof resulting from the combination of the taper associated with the second portion 168 and the configuration and orientation of the first, second, and third through-holes 190, 192, 194. The fourth, fifth and sixth indents 202, 204, 206 may be evenly spaced about the second end 162 of the intermediate link 128, and may be evenly spaced from the first, second and third indents 196, 198, 200 as shown in FIG. 8C. The fourth, fifth and sixth indents 202, 204, 206 may serve to reduce the pinching or binding of the cables when one intermediate link 128 of the second mechanism 14 is moved relative, to another intermediate link 128 coupled thereto.

According to various embodiments, an intermediate link 128 may also define an opening, (not shown) that extends from the second surface 172 or from one of the grooves 174, 176, 178 to the first surface 170 of the intermediate link 128, The intermediate link 128 may have any number of such openings, and any number of the intermediate links 128 may have such openings. Referring to FIGS. 2 and 4, the opening may be utilized as an exit point for a tool or instrument which may pass from the first end 24 of the multi-linked device 10 toward the second end 26 of the multi-linked device 10. For such embodiments, the respective intermediate link 128 may be positioned proximate to the second link 126 of the second mechanism 14. The opening may be oriented at any angle relative to the longitudinal axis 134 of the intermediate link 128. When the first mechanism 12 is removed from the second mechanism 14, and a relatively large tool or instrument is advanced from the first end 120 of the second mechanism 14 to the second end 122 of the second mechanism 14, sufficient room may not exist for a second tool or instrument (e.g., fiber optic cable) to pass through the second end 122 of the second mechanism 14. For such instances, the second tool or instrument may exit through an opening of one of the intermediate links 128.

With the above described structure, the first link 124 may be coupled to the intermediate link 128 by seating the second end 132 of the first link 124 in the segmented hemisphere 182 of the passage 180 of the intermediate link 128. As the convex configuration of the second end 132 of the first link 124 generally corresponds with the concave configuration of the segmented hemisphere 182 of the passage 180 of the intermediate link 128, the first link 124 may be coupled to the intermediate link 128 such that the longitudinal axis 134, the first, second and third grooves 142, 144, 146, and the first, second and third through-holes 154, 156, 158 of the first link 124 are respectively aligned with the longitudinal axis 164, the first, second and third grooves 174, 176, 178, and the first, second and third through-holes 190, 192, 194 of the intermediate link 128. The intermediate link 128 may be moved relative to the first link 124 such that the longitudinal axis 164 of the intermediate link 128 is not aligned with the longitudinal axis 134 of the first link 124. According to various embodiments, the configuration of the first link 124 and the intermediate link 128 allows for the intermediate link 128 to be moved relative to the first link 124 coupled thereto such that the longitudinal axis 134 of the first link 124 and the longitudinal axis 164 of the intermediate link 128 are up to approximately 10° out of alignment with one another. Similarly, one intermediate link 128 may be coupled to another intermediate link 128, and so on, by seating the second end 162 of one intermediate link 128 in the segmented hemisphere 182 of the passage 180 of another intermediate link 128. As the convex configuration of the second end 162 of the intermediate link 128 generally corresponds with the concave configuration of the segmented hemisphere 182 of the passage 180 of the intermediate link 128, the intermediate links 128 may be coupled such that the respective longitudinal axes 164, the respective first, second and third grooves 174, 176, 178, and the respective first, second and third through-holes 190, 192, 194 of the intermediate links 128 are aligned. The coupled intermediate links 128 may be moved relative to one another such that the respective longitudinal axes 164 of the coupled intermediate links 128 are not aligned. According to various embodiments, the configuration of the coupled intermediate links 128 allows for one intermediate link 128 to be moved relative to another intermediate link 128 coupled thereto such that the respective longitudinal axes 164 are up to approximately 10° out of alignment with one another.

Figure 9A:
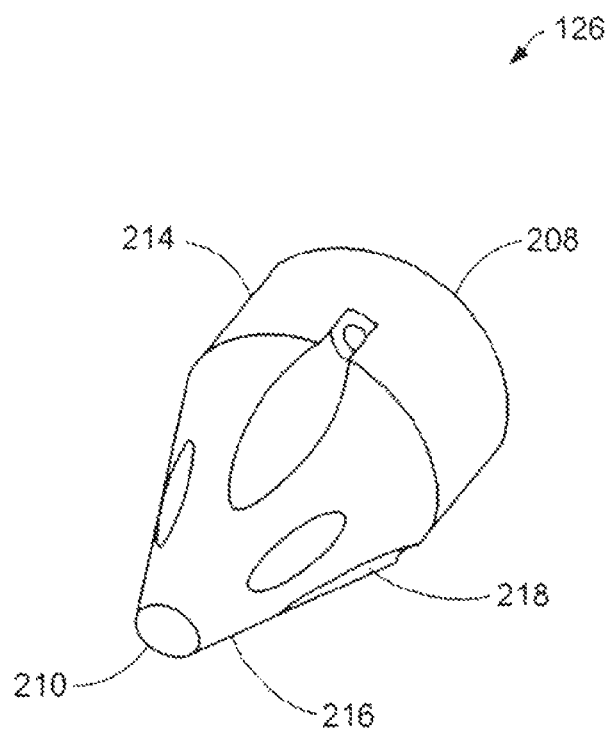
FIGS. 9A-9D illustrate various embodiments of a distal link of the sleeve mechanism.
Figure 9B:
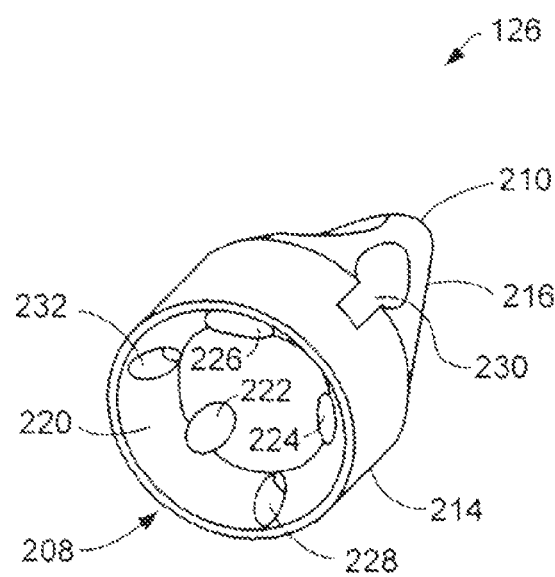
Figure 9C:
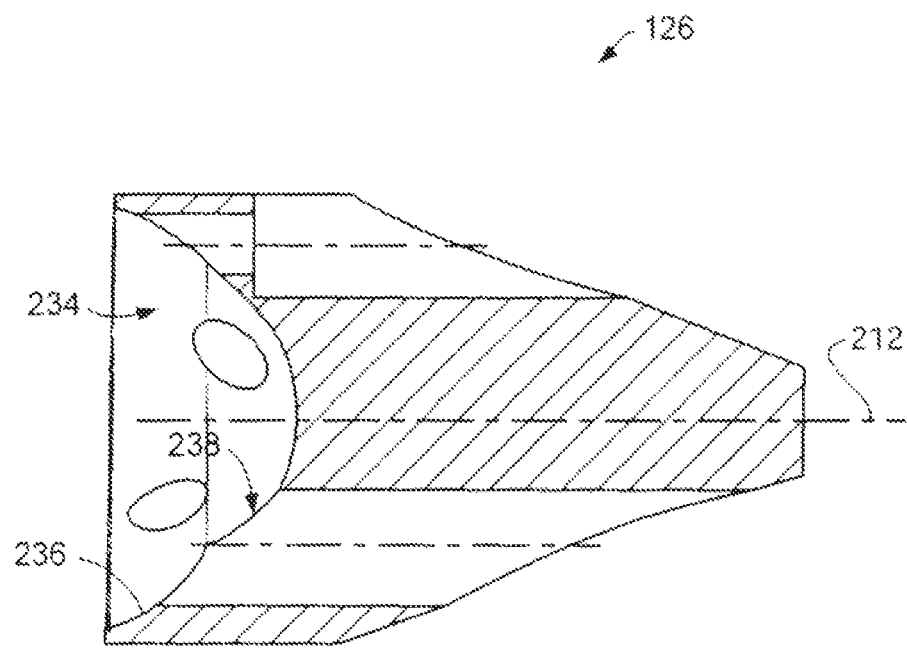

FIGS. 9A-9D illustrate various embodiments of the second link 126 (outer distal link) of the second mechanism 14. The second link 126 includes a first end 208 and a second end 210, and defines a longitudinal axis 212 that passes through the center of the first end 208 and the center of the second end 210 as shown in FIG. 9C. The second link 126 may be fabricated from any suitable material. According to various embodiments, the second link 126 is fabricated from a thermoplastic material such as, for example. Delrin®.

The second link 126 comprises a first portion 214 and as second portion 216. The first portion 214 may be considered the proximal portion and the second portion 216 may be considered the distal portion. The first portion 214 may be fabricated integral with the second portion 216. The first portion 214 has a generally cylindrical shaped exterior, and extends from the first end 208 of the second link 126 toward the second end 210 of the second link 126. According to various embodiments, the diameter of the first portion 214 is on the order of approximately 4.80 millimeters.

According to various embodiments, the second portion 216 has a generally cylindrical shaped exterior where it contacts the first portion 214, and tapers toward the second end 210 of the second link 126. The exterior of the second portion 216 is configured in the form of a generally segmented cone. According to various embodiments, the exterior of the second portion 216 tapers from the first portion 214 to the second end 210 of the second link 126 at an angle on the order of approximately 20° relative to the exterior of the first portion 214. The length of the second link 126 may be on the order of approximately 15 millimeters. However, one skilled in the art will appreciate that the length of the second link 126 can vary based on the application.

The second link 126 also comprises a first surface 218 that extends from the first end 208 of the second link 126 to the second end 210 of the second link 126, and a second surface 220 that extends from the first end 208 of the second link 126 toward the second end 210 of the second link 126. The first surface 218 may be considered the outer surface of the second link 126, and the second surface 220 may be considered the inner surface of the second link 126.

Figure 9D:
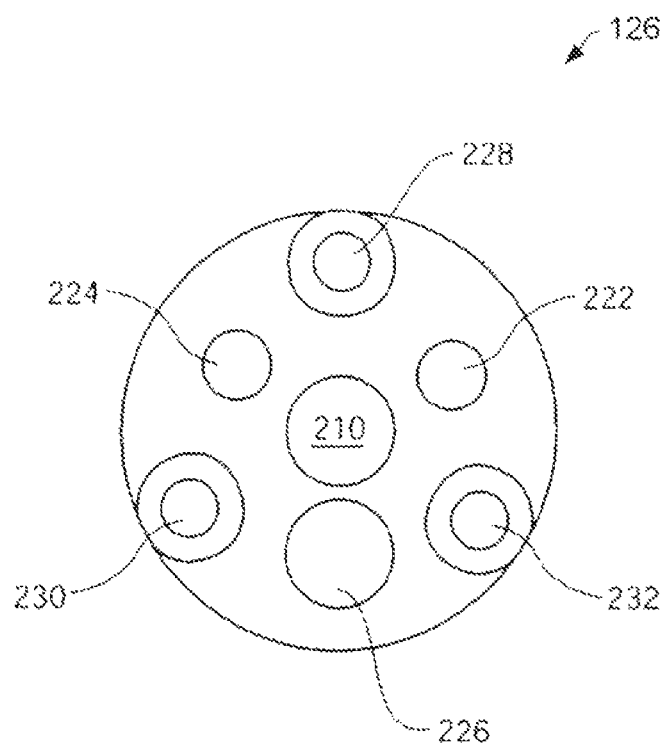

The second link 126 also defines a first port 222, a second port 224, and a third port 226. (See FIG. 9B). The first port 222 extends from the second surface 220 to the first surface 218 and is substantially parallel to the longitudinal axis 212. The second port 224 extends from the second surface 220 to the first surface 218 and is substantially parallel to the longitudinal axis 212. The third port 226 extends from the second surface 220 to the first surface 218 and is substantially parallel to the longitudinal axis 212. The first, second and third ports 222, 224, 226 may be cylindrical shaped and may be evenly spaced about the longitudinal axis 212 of the second link 126 as shown in FIG. 9D. The size of each of the ports 222, 224, 226 may be identical to one another or may be different from one another. For example, according to various embodiments, the first and second ports 222, 224 are configured as cylinders having diameters on the order of approximately 1.50 millimeters, and the third port 226 is configured as a cylinder having a diameter on the order of approximately 2.50 millimeters. Other dimensions are possible. The first, second and third ports 222, 224, 226 are each configured to receive and surround any of a variety of tools or instruments (e.g., ablation tools) which may pass from the first end 24 of the multi-linked device 10 to the second end 26 of the mufti-linked device 10.

The second link 126 also defines a first through-hole 228, a second through-hole 230, and a third through-hole 232. (See FIG. 9B). The first through-hole 228 extends from the second surface 220 to the first surface 218 and is substantially parallel to the longitudinal axis 212. The second through-bole 230 extends from the second surface 220 to the first surface 218 and is substantially parallel to the longitudinal axis 212. The third through-hole 232 extends from the second surface 220 to the first surface 218 and is substantially parallel to the longitudinal axis 212. The first, second and third through-holes 228, 230, 232 are generally cylindrical shaped. According to various embodiments, the through-holes 228, 230, 232 are evenly spaced from one another as shown in FIG. 9D. The size of each of the through-holes 228, 230, 232 may be identical to one another or may be different from one another. For example, according to various embodiments, the respective diameters associated with the through-holes 228, 230, 232 may each be on the order of approximately 1.25 millimeters. The first through-hole 228 is configured to receive and surround a cable. The second through-hole 230 is configured to receive and surround a cable. The third through-hole 232 is configured to receive and surround a cable.

The second link 126 also defines a recess 234 that extends from the first end 208 toward the second end 210 along the longitudinal axis 212 as shown in FIG. 9C. According to various embodiments, the recess 234 is generally configured as a complex shape that comprises a combination of a first segmented hemisphere 236 that extends from the first end 208 toward the second end 210, and a second segmented hemisphere 238 that extends from the first segmented hemisphere 236 toward the second end 210 of the second link 126. According to various embodiments, the first segmented hemisphere 236 represents a portion of a sphere having a diameter on the order of approximately 9.50 millimeters, and the second segmented hemisphere 238 represents a portion of a sphere having a diameter on the order of approximately 7.0 millimeters. The first segmented hemisphere 236 of the recess 234 is configured to receive the second end 162 of an intermediate link 128 when the intermediate link 128 is coupled to the second link 126.

With the above described structure, an intermediate link 128 may be coupled to the second link 126 by seating the second end 162 of the intermediate link 128 in the first segmented hemisphere 236 of the recess 234 of the second link 126. As the convex configuration of the second end 162 of the intermediate link 128 generally corresponds with the concave configuration of the first segmented hemisphere 236 of the recess 234 of the second link 126, the intermediate link 128 may be coupled to the second link 126 such that the longitudinal axis 164, the first, second and third grooves 174, 176, 178, and the first, second and third through-holes 199, 194 of the intermediate link 128 are respectively aligned with the longitudinal axis 212, the first, second and third ports 222, 224, 226, and the first, second and third through-holes 228, 230, 232 of the second link 126. The second link 126 may be moved relative to the intermediate link 128 coupled thereto such that the respective longitudinal axes 164, 212 are not aligned. According to various embodiments, the configuration of the second link 126 allows for an intermediate link 128 coupled thereto to be moved relative to the second link 126 such that the respective longitudinal axes 164, 212 are up to approximately 10° out of alignment with one another.

When the first mechanism 12 is inserted into the second mechanism 14, the first second and third grooves 70, 72, 74 of the intermediate links 32 of the first mechanism 12 may be substantially aligned with the first, second and third grooves 174, 176, 178 of the intermediate links 128 of the second mechanism 14, and the first, second and third grooves 98, 100, 102 of the second link 30 of the first mechanism 12 may be substantially aligned with the first, second and third ports 222, 224, 226 of the second link 126 of the second mechanism 14. The combination of the first grooves 70 of the intermediate links 32 of the first mechanism 12 aligned with the first grooves 174 of the intermediate links 128 of the second mechanism 14 allows the respective first grooves 70, 174 to collectively serve as a first working port that is substantially aligned with the first port 222 of the second link 126 of the second mechanism 14. The first groove 70 may be considered the inner portion of the first working port and the first groove 174 may be considered the outer portion of the first working port.

Similarly, the combination of the second grooves 72 of the intermediate links 32 of the first mechanism 12 aligned with the second grooves 176 of the intermediate links 128 of the second mechanism 14 allows the respective second grooves 72, 176 to collectively serve as a second working port that is substantially aligned with the second port 224 of the second link 126 of the second mechanism 14, and the combination of the third grooves 74 of the intermediate links 32 of the first mechanism 12 aligned with the third grooves 178 of the intermediate links 128 of the second mechanism 14 allows the respective third grooves 74, 178 to collectively serve as a third working port that is substantially aligned with the third port 226 of the second link 126 of the second mechanism 14. The second groove 72 may be considered the inner portion of the second working port and the second groove 176 may be considered the outer portion of the second working port. The third groove 74 may be considered the inner portion of the third working port and the third groove 178 may be considered the outer portion of the third working port. The first, second and third working ports may be utilized to pass various tools or instruments (e.g., ablation tools) from the first end 24 of the multi-linked device 10 to the second end 26 of the multi-linked device 10. For the exemplary sizes described hereinabove, the third working port is larger than the first and second working ports. Accordingly, the third working port may be utilized to can a particular tool or instrument that is too large to be carried by the first or second working ports.

When the respective grooves 70, 72, 74, 174, 176, 178 of the respective intermediate links 32, 128 are aligned and collectively surround the various tools and instruments, the combination of the grooves 70, 72, 74, 174, 176, 178 and the tools and instruments may serve to limit or prevent the rotation of the first mechanism 12 relative to the second mechanism 14.

As the diameter of the passage 180 of the intermediate link 128 of the second mechanism 14 is larger than the diameter of any portion of the first mechanism 12, a three-dimensional space 240 exists between the first mechanism 12 and the second mechanism 14 when the first mechanism 12 is received by the second mechanism 14 (See FIG. 1B). According to various embodiments, the space 240 may be utilized to carry wiring, tools, instruments, etc. from the first end 24 of the multi-linked device 10 toward the second end 26 of the multi-linked device 10.

According to various embodiments, one or more steering cables may be fabricated from any suitable material. For example, according to various embodiments, the steering cables may be fabricated from a polyethylene fiber cable such as, for example. Spectra®. The steering cables may be utilized to control the movement of the multi-linked device 10. For example, by applying a substantially equal tension to each of the steering cables, the first mechanism 12 and/or second mechanism 14 may be steered in a direction such that the respective longitudinal axes 38, 62, 90, 134, 164, 212 of each of the links 28, 30, 32, 124, 126, 128 are all aligned. By applying a different tension to one or more of the steering cables, the first mechanism 12 and/or the second mechanism 14 may be steered in a direction such that the respective longitudinal axes 38, 62, 90, 134, 164, 212 of each of the links 28, 39, 32, 124, 126, 128 are not all aligned. The cables 16, 18, 20 may also be utilized to control the relative state of the second mechanism 14. For example, when a uniform tension is applied to the steering cables, the second mechanism 14 may be placed in a "rigid" state, and when a tension is removed from the steering cables, the second mechanism 14 may be placed in a "limp" state. According to various embodiments, one or more of the steering cables may be attached at the first end 130 of the first link 124 of the second mechanism 14 to respective pullies (not shown) by, for example, respective stopper knots. The steering cables may be attached to the second end 132 of the second link 126 of the second mechanism 14 by, for example, respective stopper knots. One skilled in the art will appreciate that, according to other embodiments, the "rigid" and "limp" states may be achieved by subjecting the first and/or second mechanisms 12, 14 to a twisting force, or by any other manner known in the art.

According to various embodiments, one or more tensioning cables may be fabricated from any suitable material. For example, according to various embodiments, the tensioning cables may be fabricated from a polyethylene fiber cable such as, for example, Spectra®. The tensioning cables may be utilized to control the relative state of the first mechanism 12. For example, when the tensioning cable is drawn tight, the first mechanism 12 may be placed in a "rigid" state, whereas when the tensioning cable is let loose, the first mechanism 12 may be placed in a "limp" state. According to various embodiments, the tensioning cable may be attached at the first end 34 of the first link 28 of the first mechanism 12 to a pulley (not shown) by, for example, a stopper knot. The tensioning cable may be attached to the second end 88 of the second link 30 of the first mechanism 12 by, for example, a stopper knot.

Figure 10:
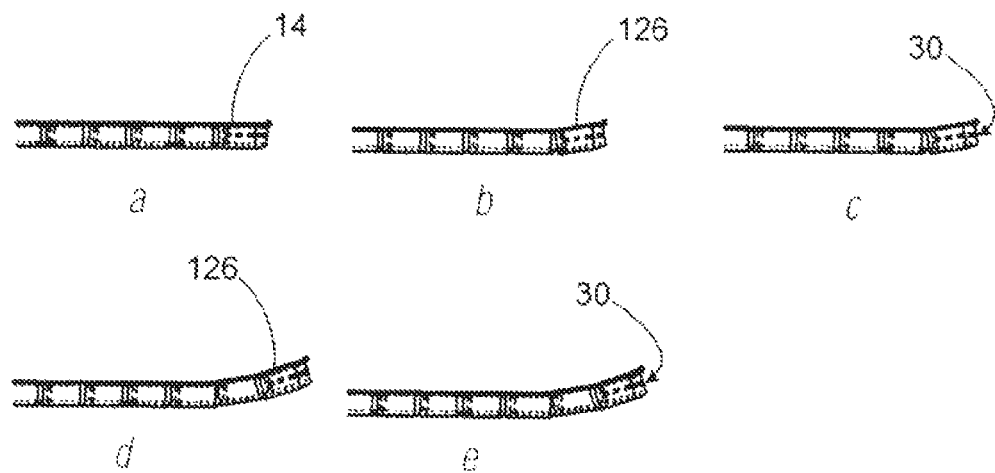
FIG. 10 illustrates various embodiments of a motion sequence of the device of FIG. 1.

FIG. 10 illustrates various embodiments of a motion sequence of the steerable multi-linked device 10. At the start of the sequence, the second mechanism 14 surrounds the first mechanism 12 as shown in step "a" of FIG. 10, the longitudinal axes 38, 62, 90 of the links 28, 30, 32 of the first mechanism 12 are substantially aligned with the respective longitudinal axes 134, 164, 212 of the links 124, 126, 128 of the second mechanism, and the second end 26 of the first mechanism 12 is at substantially the same position as the second end 122 of the second mechanism 14. A tensioning cable is pulled tight, thereby placing the first mechanism 12 in the rigid mode. The steering cables are not pulled tight, thereby placing the second mechanism 14 in the limp mode.

The second mechanism 14 is then advanced so that its second link 126 is positioned approximately one link ahead of the second end 24 of the first mechanism 12 as shown in step "b" of FIG. 10. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the steering cables are pulled with identical force in order to place the second mechanism 14 in the rigid mode, thereby preserving, the position and orientation of the second mechanism 14.

The pulling force of the tensioning cable is then released to place the first mechanism 12 in the limp mode. After the first mechanism 12 is placed in the limp mode, the first mechanism 12 is advanced so that its second link 30 is at substantially the same position as the second end 122 of the second mechanism 14 as shown in step "c" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12.

The pulling forces of the steering cables are then released to place the second mechanism 14 back in the limp mode. After the second mechanism 14 is placed back in the limp mode, the second mechanism 14 is advanced so that its second link 126 is once again positioned approximately one link ahead of the second end 26 of the first mechanism 12 as shown in step "d" of FIG. 10. After the second link 126 is in the desired position and orientation, the steering cables are pulled, with identical force in order to place the second mechanism 14 in the rigid mode, thereby preserving the position and orientation of the second mechanism 14.

The pulling force of the tensioning cable is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12. The general motion sequence described hereinabove, may be repeated any number of times, and the second link 126 of the second mechanism 14 may be advancing in any direction and orientation. One skilled in the art will appreciate that any number of motion sequences may be utilized with the multi-linked device 10. For example, according to various embodiments, the second mechanism 14 may advance any number of links ahead of the first mechanism 12.

The exemplary sizes described hereinabove are generally relative to each other, and one skilled in the art will appreciate that the multi-linked device 10 can be scaled up or scaled down. For example, although the diameter at the largest portion of the intermediate link 128 of the multi-linked, device 10 is on the order of approximately 9.65 millimeters for the embodiments described hereinabove, one skilled in the art will appreciate that, for other embodiments, the intermediate link 128 can be scaled down such that the diameter at the largest portion of the intermediate link 128 of the multi-linked device 10 is on the order of approximately 1.0 millimeter. For such embodiments, each of the other components of the multi-linked device 10 would also be proportionally scaled down.

Figure 11:
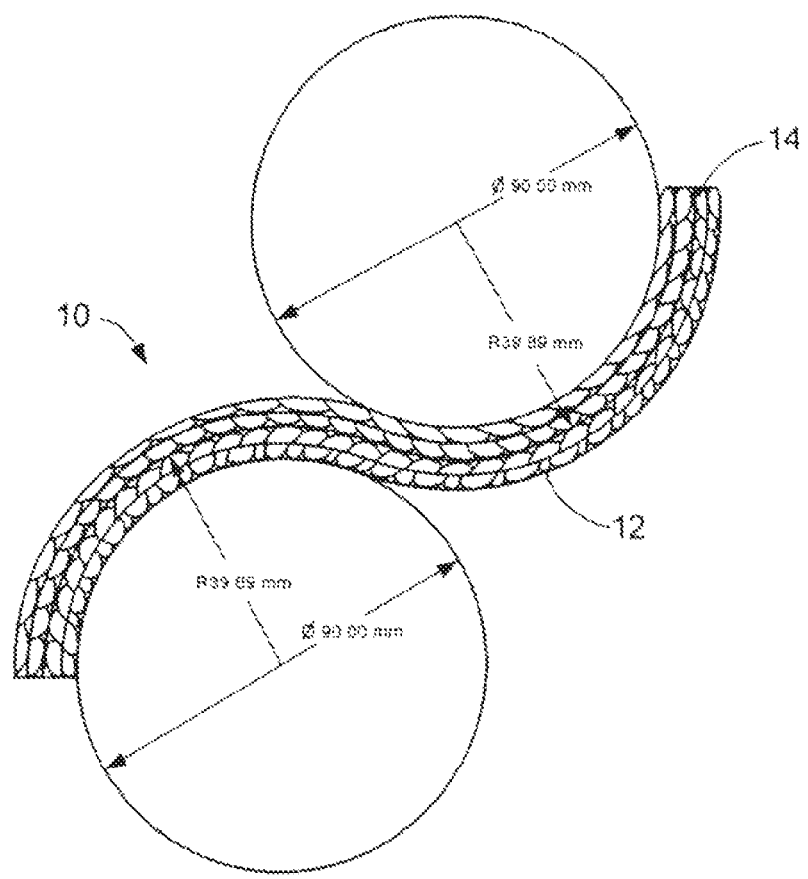
FIG. 11 illustrates various embodiments of a steerable multi-linked device traversing a path having tight curvatures.

The combination of the unique configuration of the respective links 28, 30, 32 winch comprise the first mechanism 12 and the unique configuration of the respective links 124, 126, 128 which comprise the second mechanism 14 provides the multi-linked device 10 with the ability to traverse a path defined by the circumference of a circle having a relatively small radius. For example, for the exemplary sizes described hereinabove, the multi-linked device 10 can traverse a path defined by the circumference of a circle having a radius on the order of approximately 45 millimeters. An example of the multi-linked device 10 navigating such tight curvatures is shown in FIG. 11. For embodiments, where the largest portion (e.g., measured at the outer diameter) of the intermediate link 128 of the multi-linked device 10 is on the order of approximately 1.0 millimeter, the multi-linked device 10 can traverse a path defined by the circumference of a circle having a radius significantly smaller than 45 millimeters. It may also be possible to achieve a smaller radius of curvature independently of reducing outer diameter. For example, changing the longitudinal dimension (e.g., length of an intermediate link), the radius of curvature may be reduced while maintaining a constant outer diameter. One skilled in the an will appreciate that the ability to navigate such tight curvatures makes the multi-linked device 10 suitable for use in a number of different minimally invasive procedures, both in luminal spaces and in intracavity spaces.

In an embodiment, the steerable multi-linked device may include a spherical distal assembly. The assembly includes at least two components, typically a distal link cup and a sphere. The sphere is a separate component from the distal link cup, and is connected to a separate control system than the multi-linked device. This separate control system includes a set of auxiliary actuation cables as well as additional control elements. The auxiliary actuation cables may be connected to the sphere as well as the additional control elements, and the additional control elements may alter the lengths of the auxiliary actuation cables, resulting in movement of the sphere. The separate control system may be located in the feeder as discussed above, or in the multi-linked device.

The sphere is kinematically constrained from translation in the x-direction and y-direction (of a three dimensional coordinate system originating from the distal link cap where the z-axis points forward, i.e., is the longitudinal axis of the distal link cup and the x-axis and y-axis are perpendicular to the z-axis) by the shape of the distal link cup, and is constrained in the z-direction by the auxiliary actuation cables. The sphere is also constrained from rotation about the longitudinal axis of the distal link cup (z-axis) by the auxiliary actuation cables, but the sphere may rotate about the two axes orthogonal to the z-axis.

The inclusion of the spherical distal assembly extends the range of motion of the distal tip of the multi-linked device. However, it is important to note that the sphere need not be connected to the multi-link device. Tension on the auxiliary actuation cables kinematically constrains the sphere in the distal link cup, thereby forming the distal link assembly. A steerable multi-linked device with a distal link cup may function normally without the sphere; however, the sphere will not function without the distal link cup and auxiliary actuation cables. The spherical distal assembly is described below in more detail with regards to FIGS. 12-14.

Figure 12:
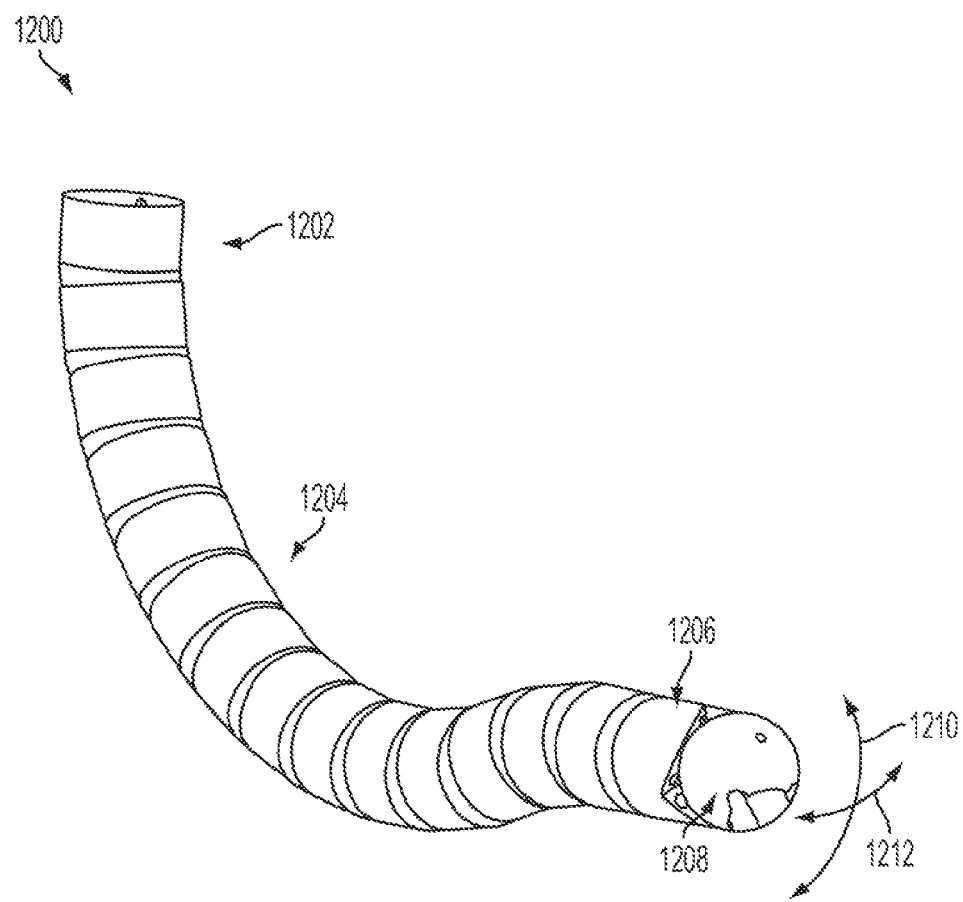
FIG. 12 illustrates various embodiments of a steerable multi-linked device having a spherical distal assembly.

FIG. 12 illustrates an exemplary embodiment of multi-linked device 1200. Similar to embodiments represented above (e.g., the embodiment illustrated in FIG. 2), multi-linked device 1200 has a proximal link 1202 and a series of intermediate links 1204. Device 1200 also has a spherical distal link cup 1206 and a spherical link 1208, which combine to form the spherical distal assembly. As shown in FIG. 12, the spherical link of device 1200 has a significantly wider range of motion than the relative motion at the intermediate links and the distal link cup (represented by arrows 1210 and 1212) for orientating a device (e.g., a camera) mounted in spherical link 1208, or a device passing through one of the ports of the multi-linked device (e.g., and ablation catheter). In alternative embodiments, the spherical link may have a range of motion similar to or narrower than the motion of the intermediate links and the distal link cup.

Movement of device 1200 is similar to the movement of device 12 as discussed above. A number of steering cables (in this example, three steering cables) are directed through holes in each link to the spherical distal link cup 1206 where the cables are terminated. Similar to before, by changing the length of each steering cable (e.g., by changing the tension on each cable, thus changing the length), the distal link of device 1200 may be oriented in a specific direction. Control of spherical link 1208 is achieved through an additional set of auxiliary actuation cables. These auxiliary actuation cables may be directed through either the same set of holes as the steering cables, or a separate set of holes in each link and are terminated on spherical link 1208. Each link of device 1200 (i.e., proximal, intermediate, and spherical distal assembly) and the associate cable holes and cable terminations are discussed in greater detail with respect to FIGS. 13A-14.

Figure 13A:
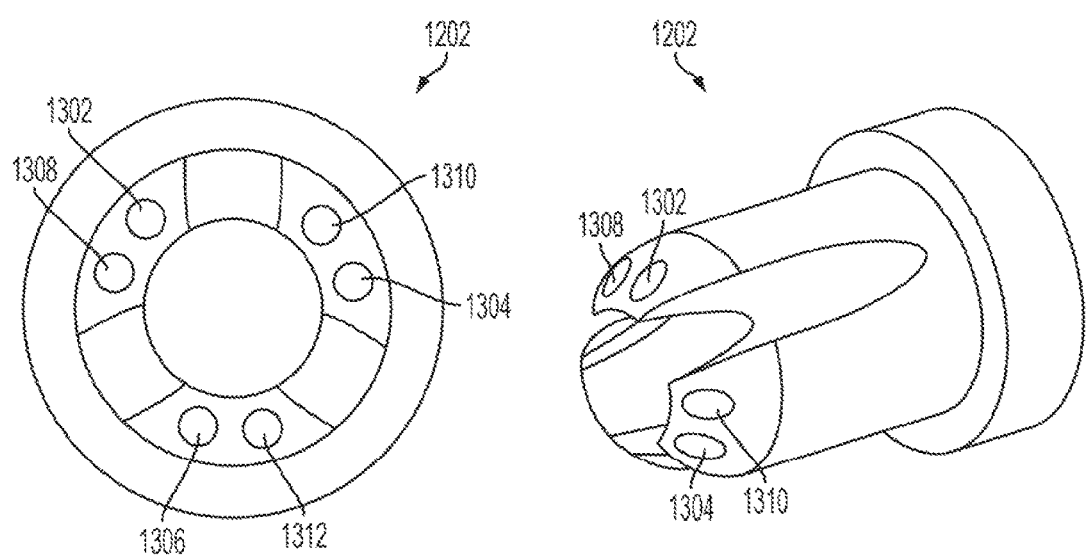

FIG. 13A illustrates multiple views of proximal link 1202, a cross-sectional view and an isometric view of the link. Proximal link 1202 functions similarly to proximal link 124 as discussed above and illustrated in FIGS. 7A-7C. Proximal link 1202 differs from link 124 though as proximal link 1202 includes six holes to accommodate the cables, e.g., holes 1302, 1304 and 1306 for accommodating the three steering cables, and holes 1308, 1310 and 1312 for accommodating the auxiliary actuation cables. However, it should be recognized that this arrangement is merely shown by way of example. Any configuration of holes that provides protection for the cables while still maintaining link integrity may be used, for example, three total holes wherein each hole accommodates two separate cables, one cable for steering the multi-linked device and one auxiliary actuation cable, such as the arrangement illustrated in FIG. 7C, where proximal link 124 has three holes 154, 156 and 158. Using this arrangement, however, may cause friction between the two sets of cables and require a coating be applied to each cable to prevent any damage to the cables caused by friction. Similarly, each cable may be housed in a low friction sheath that would limit the friction caused due to cables sharing a hole. According to various embodiments, proximal link 1202 is fabricated from a thermoplastic material such as, for example, Delrin®, or any suitable metal such as aluminum or stainless steel.

Figure 13B:
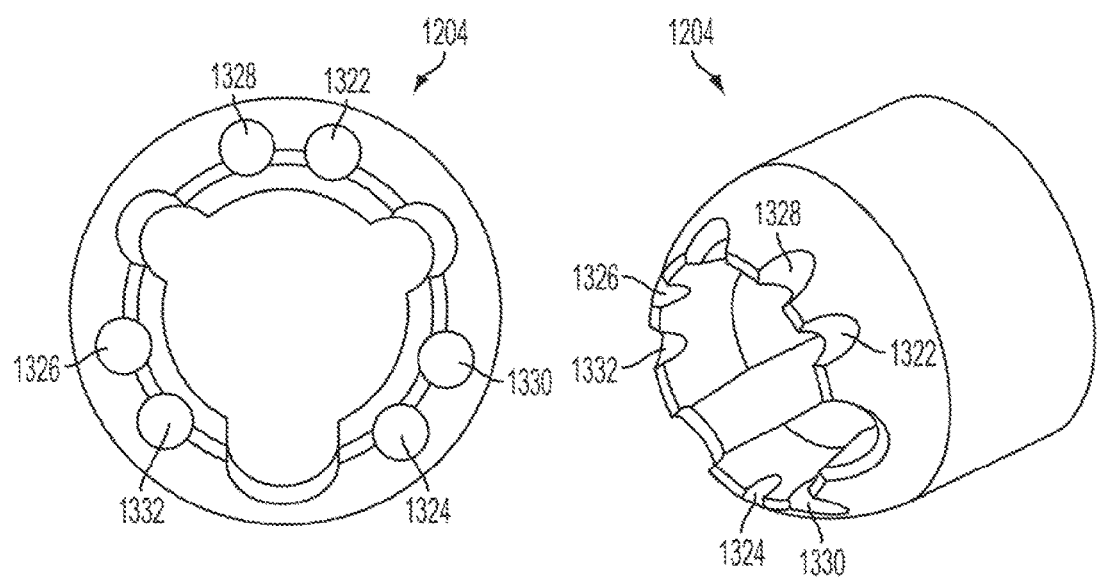

FIG. 13B illustrates multiple views of intermediate link 1204, a cross-sectional view and an isometric view of the link. Intermediate link 1204 functions similarly to intermediate link 128 as discussed above and illustrated in FIGS. 8A-8C. Intermediate link 1204 differs from link 128 though as intermediate link 1204 includes six holes to accommodate the cables, e.g., holes 1322, 1324 and 1326 for accommodating the three steering cables, and holes 1328, 1330 and 1332 for accommodating the auxiliary actuation cables. However, it should be recognized that this arrangement is merely shown by way of example. Any configuration of holes that provides protection for the cables while still maintaining link integrity may be used, for example, three total holes wherein each hole accommodates two separate cables, one cable for steering the multi-linked device and one auxiliary actuation cable, such as the arrangement illustrated in FIG. 7C, where proximal link 128 has three holes 190, 192 and 194. Using this arrangement, however, may cause friction between the two sets of cables and require a coating be applied to each cable to prevent any damage to the cables caused by friction. Similarly, each cable may be housed in a low friction sheath that would limit the friction caused due to cables sharing a hole. According to various embodiments, intermediate link 1204 is fabricated from a thermoplastic material such as, for example, Delrin®, or polysulfone.

Figure 13C:
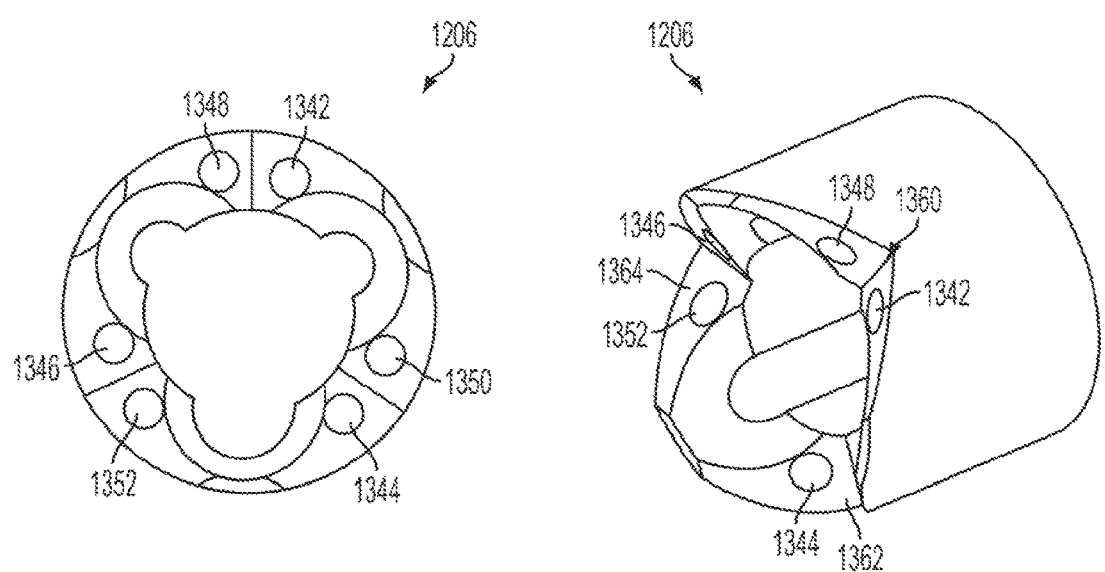
Figure 14:
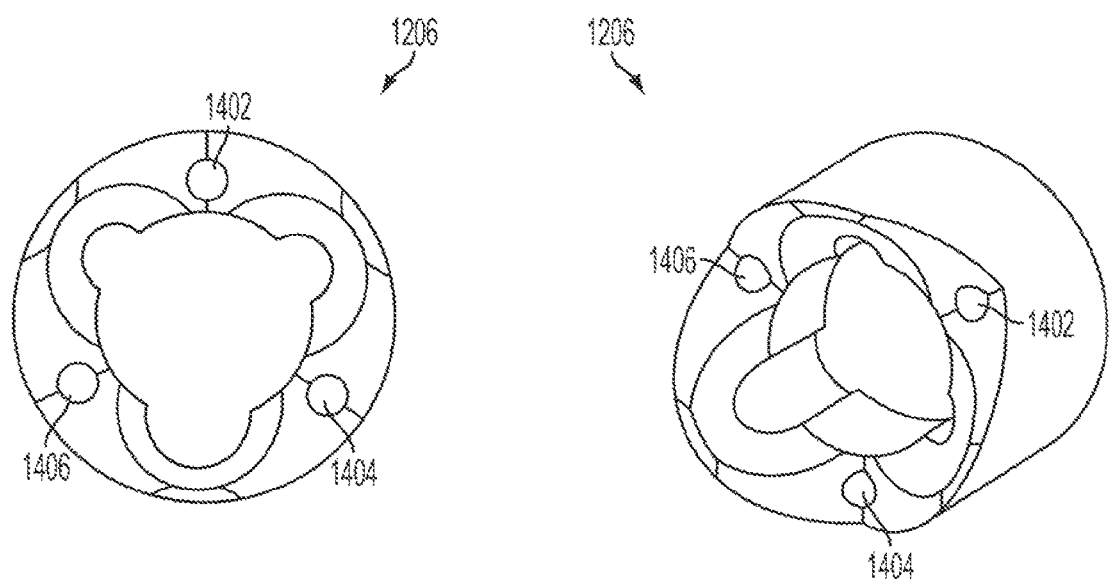
FIG. 14 illustrates an additional embodiment of a spherical distal link cup as described in FIG. 13C.

FIG. 13C illustrates multiple views of spherical distal link cup 1206, a cross-sectional view and an isometric view of the link. Spherical distal link cup 1206 is the termination point for the multi-link device steering cables. The multi-link device cables are accommodated by holes 1342, 1344 and 1346. A knot may be made in the end of the multi-link steering cables such that the end of the cable is larger than the opening of the holes. Similarly, additional termination techniques may be used, such as a mechanical clamp or splicing the cables. Once the cables are terminated at spherical distal link cup 1206, any change in length of the multi-link device steering cables is transferred directly to the spherical distal link cup 1296, thereby changing the orientation of the spherical distal assembly. In the example spherical distal cup illustrated in FIG. 13C, three separate holes 1348, 1350 and 1352 may be provided for the auxiliary actuation cables. However, as before with proximal link 1202 and intermediate link 1204, auxiliary actuation cables may share a hole with a multi-link device steering cable. FIG. 14 illustrates an example of spherical distal cup 1296 wherein three holes 1402, 1404 and 1406 are provide, wherein each hole accommodates both a steering cable as well as an auxiliary actuation cable.

Spherical distal link cup 1206 also has three concave surfaces (e.g., 1360, 1362 and 1364 in FIG. 13C). These concave surfaces may have as radius similar to the radius of the spherical link to insure a proper fit with the spherical link. According to various embodiments, spherical distal link cup 1206 is fabricated from thermoplastic material such as, for example, Delrin®, or any suitable metal such as aluminum or stainless steel.

Figure 13D:
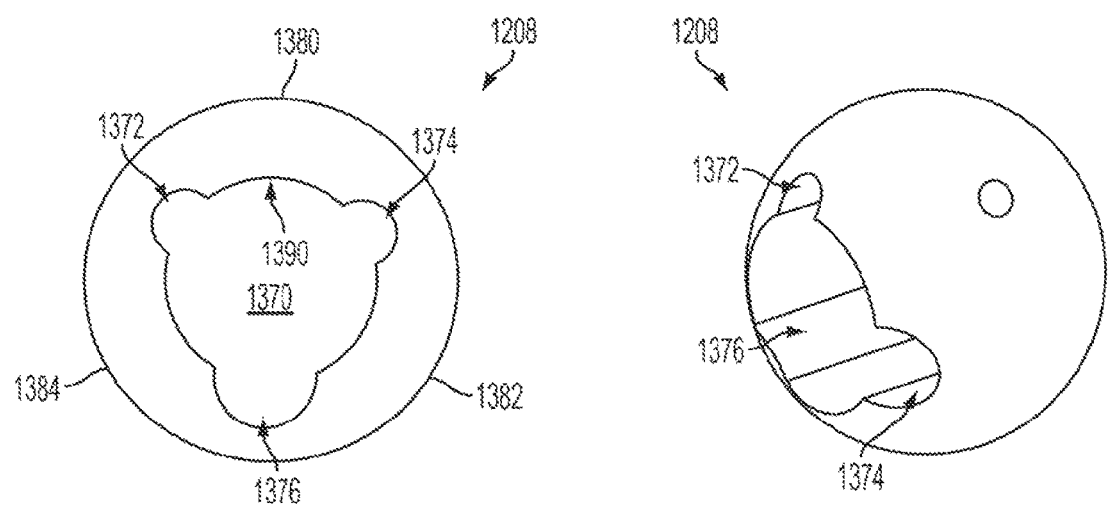

FIG. 13D illustrates multiple views of spherical link 1208, a cross sectional view and an isometric view of the link. Spherical link 1208 functions similarly to distal link 30 as discussed above. A device (e.g., a camera) may be mounted in opening 1370, similar to distal link 30, however, due to the manner of control and termination locations of the auxiliary actuation cables, spherical link 1208 provides a larger range of motion for the mounted device than distal link 30. Additionally, a medical tool (e.g., an ablation catheter) may be mounted in one of working ports 1372, 1374 and/or 1376.

Each of the auxiliary actuation cables is terminated at spherical link 1208 via holes 1380, 1382 and 1384. Each cable is run along the exterior of spherical link 1208 and fed into a hole. The cable is then knotted or otherwise terminated, at the interior of spherical link 1208 such that the auxiliary actuation cables react on the inner surface of spherical link 1208, for example, inner surface 1390. Once the auxiliary actuation cables are attached, spherical link 1208 is fitted into spherical distal link cup 1206 forming the spherical distal assembly. By applying a tension to one of the auxiliary actuation cables which thereby changes the length of the auxiliary actuation cable, spherical link 1208 rotates accordingly. As configured, spherical link 1208 is not attached to the multi-link device, rather it is kinematically constrained in spherical distal cup 1206 and is held in place by the auxiliary actuation cables.

According to various embodiments, spherical link 1208 is fabricated from a material, that is mismatched from the type of material used to fabricate spherical distal link cup 1206. For example, if spherical distal link cup 1206 is fabricated from a thermoplastic material such as, for example, Delrin®, then spherical link 1208 may be fabricated, from metal such as, for example, stainless steel or other suitable metal. By fabricating both spherical distal link cup 1206 and spherical link 1208 from mismatched materials, friction between the two is reduced. However, it should be noted that mismatched materials are not required, and in some applications (e.g., precision surgical applications) additional friction may be desired.

Figure 15:
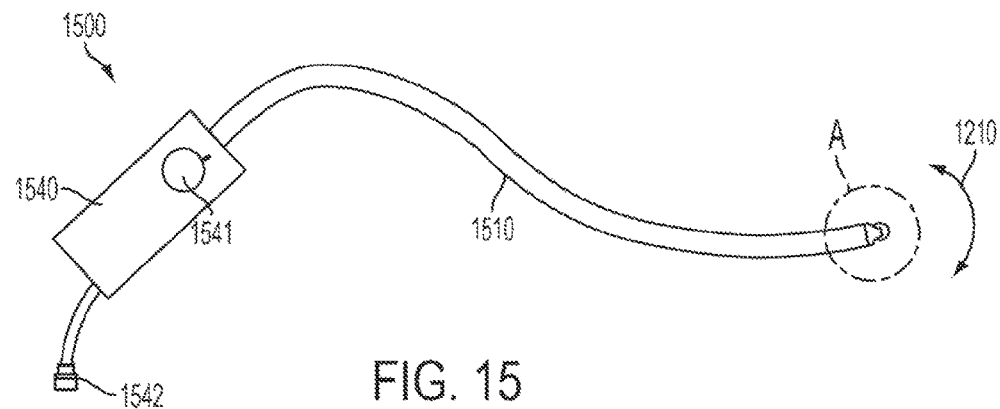
FIG. 15 illustrates various embodiments of a catheter device with a rotatable distal assembly comprising a hinge pin attachment between an adapted link and a rotating link.
Figure 15A:
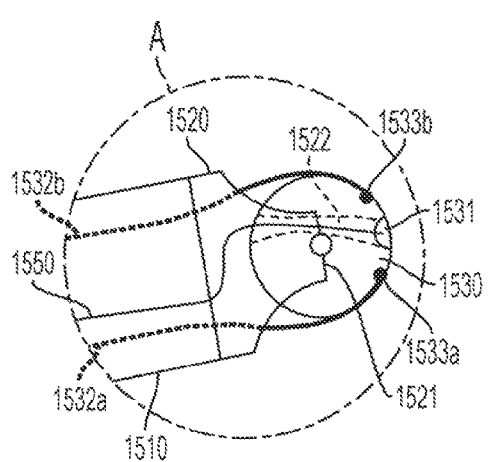
FIGS. 15A-B illustrate magnified views of the distal end of the catheter device of FIG. 15.

FIG. 15 illustrates an exemplary side view of a device according to an embodiment. As illustrated by FIG. 15, the device may include a rotating link configured to rotate with a single degree of freedom. Device 1500 may be a catheter, such as an interventional or percutaneous catheter device. Device 1500 may include a flexible catheter shaft 1510, such as a shaft made of a biocompatible elastomer or other plastic such as silicone or polyurethane. Handle 1540 may be located on the proximal end of shaft 1510 and may include a control, knob 1541 and/or a standard luer-lock access port 1542. Port 1542 may be configured to allow one or more tools to be inserted through port 1542, and through one or more working channels of shaft 1510, channels not shown but described in detail hereabove. FIG. 15A illustrates an exemplary distal end of a device 1500 according to an embodiment. Pivot assembly 1520 may be attached to the distal end of shaft 1510, such as via a glued joint or the like. Numerous attachment forms may be utilized to attach pivot assembly 1520 or other adapted links to shaft 1510. For example, one or more threads, snap fits, barbed connections, adhesive bonds, welds, frictional engagements and/or the like may be used. In a particular embodiment, one or more cables may be attached to pivot assembly 1520 and maintained in tension to maintain contact between shaft 1510 and pivot assembly 1520. In an alternative embodiment, one or more magnets or electromagnets may be included in the distal end of shaft 1510 and/or the proximal end of pivot assembly 1520, each of which may mate with a magnet or magnetic material in the corresponding part. The resulting magnetic force may maintain the pivot assembly 1520 in contact with the distal end of shaft 1510.

Pivot assembly 1520 may include a hinge pin 1521 to which rotating sphere 1530 may be rotatably attached. Two rotation cables, cables 1532*a* and 1532*b* may travel through a channel, lumen or other opening of shaft 1510, and terminate on sphere 1530 at welds 1533*a* and 1533*b* respectively. Welds 1533*a* and 1533*b* may be positioned on sphere 1530 such as to determine the amount of rotation caused as cables 1532*a* and 1532*b* are retracted proximally. The amount of rotation may be related to the positioning of the termination. For example, as oriented in FIG. 15A, as the termination moves distally, more rotation may be achieved by retracting the associated cable. As the termination approaches the distal end, and continues along, the same circumference proximally, rotational range may be further increased. Position of the exit of each cable 1532a and 1532b from pivot assembly 1520 may also determine the amount of rotation by sphere 1530. The closer the exit of cables 1532a and 1532b to the axial center of pivot assembly 1520, the greater the rotation achievable.

Holes or other pass thin locations for cables combined with cable termination sites (e.g. location on sphere 1530) and sphere versus cup diameter may determine the range of allowable rotation. In an embodiment, a first cable, a first pass thru hole and a first cable termination may be positioned to allow a range of rotational patterns all starting from a first starting position. A second cable, second pass thru hole and a second cable termination may be positioned to allow any of the range of rotational positions caused by retracting the first cable to be reversed by retracting the second cable (e.g. returned to the first starting position). In an embodiment, sphere 1530 may be rotated by retracting a first cable and a second cable simultaneously. In another embodiment, sphere 1530 may be rotated by retracting a first cable and advancing a second cable (e.g., to accommodate the rotation causes by the first cable retraction).

Holes or other pass through locations for cables combined with cable termination sites (e.g. location on sphere 1530) may be chosen to prevent the performance of a rotation to any rotational position from which advancement or retraction of one or more cables (or other action) cannot recover or otherwise depart from. In robotic engineering, this condition may be caused by a singularity. Singularities may also describe conditions in which a degree of freedom is lost, such as when joints approach a mechanical limit, e.g. when a cable reaches a mechanical stop. Singularities may be avoiding, by the repositioning of holes or termination points, or by the addition of one or more additional cables configured to move sphere 1530 from the undesired position (i.e. the additional cable adds another degree of freedom). Singularities may also be avoided with one or more features of the distal rotating assembly such as one or more ridges configured to mechanically stop rotation at one or more locations in one or more directions. Other unrecoverable positions may be avoided, such as when a first cable is wrapping around a partial circumference of a spherical portion of sphere 1530 when sphere 1530 is in a first position. If this first position is such that the path of least resistance for the first cable to follow from is different than the cable followed as it was pulled to this first position, retraction of the cable may cause an undesired rotation (e.g. during retraction the cable may slide along the surface of sphere 1530 because that was the path of least resistance). In an alternative embodiment, a singularity or other unrecoverable position may be desired, such as to cause the spherical link to rotate to such a position and remain in that position.

Figure 15B:
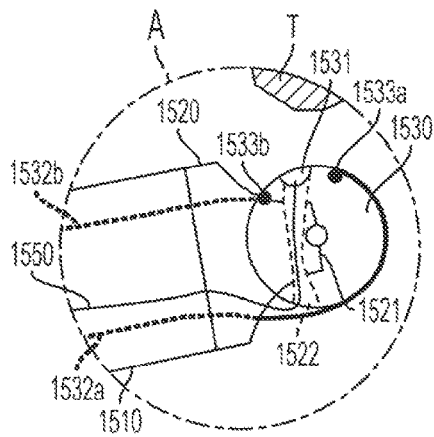

Device 1500 may include one or more tools, insertable through port 1542 of handle 1540 and advanced to pass through shaft 1510, pivot assembly 1520 and into channel 1522 of sphere 1530. Numerous medical and other tools may be inserted into device 1500 and the other devices may include, but are not limited to, cutters, graspers, dissectors, biopsy mechanisms, sensing devices such as EKG electrode or array of electrodes, energy delivery tools such as cryogenic and radiofrequency (RF) tissue ablating, tools, drug delivery devices, cameras and/or the like. As shown in FIG. 15A, ablation probe 1550 has been inserted into device 1500 and its distal end resides in channel 1522. Channel 1522 has at its distal end, an exit hole, tool port 1531 from which ablation probe 1550 can be advanced when the distal end of shaft 1510 is placed proximate a target location, and channel 1522 of sphere 1530 is rotated toward the target location. The interface of pin 1521 with sphere 1530, allows sphere 1530 to be rotated with a single degree of freedom, along lines 1210, such that channel 1522 traverses a single plane. Referring to FIG. 15B, sphere 1530 has been rotated such that advancement of ablation probe 1550 will cause the distal end of probe 1550 to travel toward target T. Target T may be a target location on a patient's heart, a tumor, or other tissue intended to be ablated in a medical procedure. Sphere 1530 has been rotated by pulling on cable 1532b and/or pushing on cable 1532a. The devices may provide a rotational link which can be oriented in numerous directions, including the radially out or 90° orientation of device 1500 illustrated by FIG. 15. Numerous procedures, such as transoral robotic surgery (TORS) procedures, may be performed with 90° and larger orientations, wherein a tool enters a conduit such as the esophagus, and exits the rotating link into the wall of the conduit relatively orthogonally. In an embodiment, an endoscope may enter a conduit such as the colon, and a tool may be advanced approximately orthogonally through the wall of the colon to perform a medical event within the wall of the colon or outside the colon.

Handle 1540 may include additional components such as additional access ports, one or more power supplies, an electronic module such as the module described in reference to FIG. 17, additional controls such as a slide or knob controlling one or more linkages, pneumatic or hydraulic assemblies and/or the like. While device FIGS. 15, 15A and 15B illustrate exemplary catheter devices 1500, additional and/or alternate devices, including, but not limited to flexible devices, such as an endoscope or multi-link device, or rigid devices, such as a laparoscopic device, may be used within the scope of this disclosure.

Figure 16:
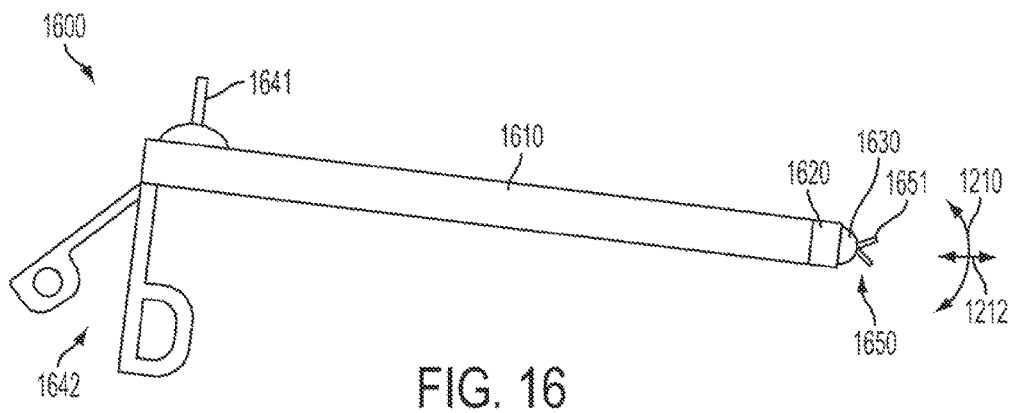
FIG. 16 illustrates various embodiments of a laparoscopic device including a scissor assembly inserted through a rotatable distal assembly.

FIG. 16 illustrates a side view of an exemplary device according to an embodiment. As illustrated by FIG. 16, a device may include a rotating link configured to rotate a cutting assembly. Device 1600 may be a laparoscopic or other similar minimally invasive medical device. Device 1600 may includes rigid tube 1610, such as a stainless steel, titanium, or other metal tube, or a non-metallic tube such as a biocompatible hard plastic tube. Cup assembly 1620 may be attached to tube 1610, such as been described above in reference to FIGS. 15, 15A and 15B. Cup assembly 1620 may be fixedly attached to tube 1610 or it may be rotatably attached. In an embodiment, cup assembly 1620 may be removably attached to tube 1610 such as to allow a different configuration cup assembly to be attached to tube 1610 and/or to allow access to the distal end of tube 1610 and/or the distal end of one or more tools advanced through tube 1610. Rotatably attached to cup assembly 1620, may be sphere 1630 which ma be configured to rotate with two degrees of freedom, along lines 1210 and 1212. At the proximal end of device 1600 may be a control, joystick 1641, which may be operably attached to two or more cables. Movement of joystick 1641 may cause sphere 1630 to move along either or both lines 1210 and 1212. In an alternative embodiment, a counter part sphere may be directly connected to the proximal end of sphere 1630 with actuation cables such that the sphere is controlled in a one-to-one motion map (spheres of equal diameter), or a scaled motion map (spheres having different diameters).

Device 1600 may include a cutting assembly which may include at its distal end, scissor assembly 1650 shown exiting sphere 1630. Scissor assembly 1650 may include blades 1651 which may rotate with the rotation of sphere

1639, along one or both lines 1210 and 1212. Also at the proximal end of device 1600 may be a scissor handle-like mechanism, actuator 1642. Opening and closing of actuator 1642 may cause the correlating opening and closing of blades 1651, such as via a mechanical, pneumatic, hydraulic or other applicable linkage that may be operably connected between actuator 1642 and scissor assembly 1650.

FIG. 17 illustrates a side sectional view of an exemplary distal portion of a device. As illustrated by FIG. 17, a distal portion may include a distal cup configured to rotatably interface with a more proximal spherical surface and/or means for transferring power, such as electrical current, or data to a rotating distal member. In an embodiment, power and/or data may be transmitted using one or more lines, wires, cables and/or the like. Device 1700 may include shall 1710, such as a shaft similar to shaft 1510 of FIG. 15, 15A or 15B, tube 1610, such as that of FIG. 16, or a shall of the multi-link devices of FIGS. 1 through 14. Shaft 1710 may include partial sphere 1720, which may be fixedly or removably attached to shaft 1710. Partial sphere 1720 may be maintained in position with the distal end of shaft 1710 with one or more cables. The concave surface of the rotating cup 1730 may be rotatably engaged with the convex surface of partial sphere 1720. Cable 1732*a* and cable 1732*b* are attached at their distal ends to cup 1730 at joint 1733*a* and 1733*b* respectively, and at their proximal ends to a handle. Joint 1733*b* may be attached to surface 1738' of rotating cup 1730. The moment arm achieved with this location may be less than the moment arm that would be achieved if joint 1733*a* was located on surface 1738" of rotating cup 11730. The rotation angle per unit length of a retraction of cable 1732*b* may be greater with joint 1733 on surface 1738 versus on surface 1738". In addition, as cable 1732*b* is retracted, surface 1738' may eventually make contact with the distal end of shaft 1710, stopping the rotation. By varying the surface geometry of the adapted links and rotating links of the device (e.g. concave versus convex), the performance and other mechanical properties of the rotating mechanism may be customized. The various configurations of the distal rotating assemblies described herein may be applied to achieve varied performance such as rotation magnitude versus cable retraction and rotational force versus cable retraction force.

In an embodiment, a knot, adhesive ball, splice, mechanical crimp, and/or other cable enlarging means may be formed. In the end of a multi-link cable such that the end of the cable is larger than a hole through which the cable passes (e.g. a thru hole in rotating cup 1730). Similarly, termination techniques may be used to attach the cable end directly such as a weld, an adhesive joint, frictional engagement between the cable and a capture element, such as a v-shaped or spring-loaded capture device, a loop at the end of a cable that is fastened by way of a hook or threaded hole and screw and/or other joint forming means. In additional to cable 1732*a* and 1732*b*, one or more other cables may be provided, such as to rotate cup 1730 in alternative orientations and/or to reverse one or more rotational directions.

Partial sphere 1720 includes a first conductive element 1725, which may be configured to electrically attach to a second conductive element 1739 which may be integral to cup 1730 (i.e. similar to a slip ring connection used to transfer electrical signals or power from a rotating frame of reference to a stationary frame of reference). Conductive element 1725 may be attached to wire 1726. In an embodiment, conductive elements 1725 and 1739 may include multiple, isolated or otherwise independent conductive elements e.g. multiple aligned conductive strips separated by one or more insulators), and wire 1726 may include multiple independent wires, such that multiple independent electrical transmissions may be communicated from first conductive element 1725 to second conductive element 1739. In a preferred embodiment, wire 1726 transmits electrical energy and/or data to electronic module 1737 via first conductive element 1725, second conductive element 1739, and wire 1736 respectively. Electronic module 1737 may include energy storage means, such that cup 1730 may have an available energy source when wire 1726 is not transmitting energy, such as when wire 1726 is transmitting data to or from electronic module 1737. The electrical energy transferred can be stored and/or used by electronic module 1737 or another component within or in proximity to cup 1730. Data transmitted or received may be rotational position control or position feedback signals respectively, or numerous other forms of data such as data sent to one or more tools of device 1700, or data received from one or more sensors of device 1700.

Electronic module 1737 may be a simple or complex electrical circuit configured to perform one or inure functions such as to record data from one or more sensors, not shown but integral to cup 1730, sphere 1720 or shaft 1710. Module 1737 may include various electronic and electro-mechanical components or systems including but not limited to digital to analog converters, analog to digital converters, microcontrollers, microprocessors, multiplexers and demultiplexers, switching circuitry, MEMS circuitry and componentry/memory devices such as RAM and ROM and/or the like. Module 1737 may include one or more software programs embedded therein, such as software activated by a user during, use of a device. Module 1737 may be configured to operate and/or receive data from one or more tools, such as a camera assembly including cameras 1752*a* and 1752*b*. Cameras 1752*a* and 1752*b* are connected to electronic module 1737 via wires 1735*a* and 1735*b*. Wires 1735*a* and 1735*b* may be conductive wires, or other power and/or data conduits such as fiber optic cables. In an embodiment, cameras 1752*a* and 1752*b* may be lens assemblies, wires 1735*a* and 1735*b* may be fiber optic cables, and the optical information may be captured in a camera module integrated to electronic module 1737.

Device 1700 may include one or more medical or other tools, such as biopsy device 1751 shown in FIG. 17, as passing through shaft 1710, through partial sphere 1720 and into an opening of cup 1730, tool port 1731. As cup 1730 is rotated, by advancing and/or retracting cable 1732*a* and/or 1732*b*, or other cables not shown, the trajectory of tool port 1731 may be correspondingly rotated, such as control the trajectory of an advanced or yet to be advanced biopsy device 1751.

FIGS. 18A and 18B illustrate a top view of an exemplary adapted link, and a side sectional view of an exemplary device according to an embodiment. As shown in FIG. 18A, cup assembly 1820 may include a curvilinear groove 1824 which may be configured to guide the rotation of a rotating link, including a pin or other mating protrusion, in a preferred rotational pattern. Cup assembly 1820 may include an opening for passage of one or more wires or cables, slot 1823. Referring to FIG. 18B, device 1800 may include tube 1810 having one or more constructions or configurations as has been described in detail hereabove. The distal end of tube 1810 may include integral cup assembly 1820, which may include a concave surface and providing an adapted link. Of similar diameter and matingly received by the concave surface of cup assembly 1820, may be the convex surface of rotating sphere.

Cable 1832 may be configured to allow electrical signals or power to be transmitted from the proximal end of device 1800 to one or more components integral to tube 1810, cup assembly 1820, sphere 1830, or other component of device 1800. Cable 1832 may be electrically attached to the proximal end of wire 1852 which may be attached at its distal end to electrode 1851, shown on the distal end of sphere 1830. When sphere 1830 is rotated in a predetermined rotational pattern or otherwise, electrode 1851 may be correspondingly rotated such as to be oriented toward a target such as a particular tissue target within a patient. Device 1800 may include a handle at its proximal end. The handle may include one or more controls operably connected to cable 1832.

Figure 19:
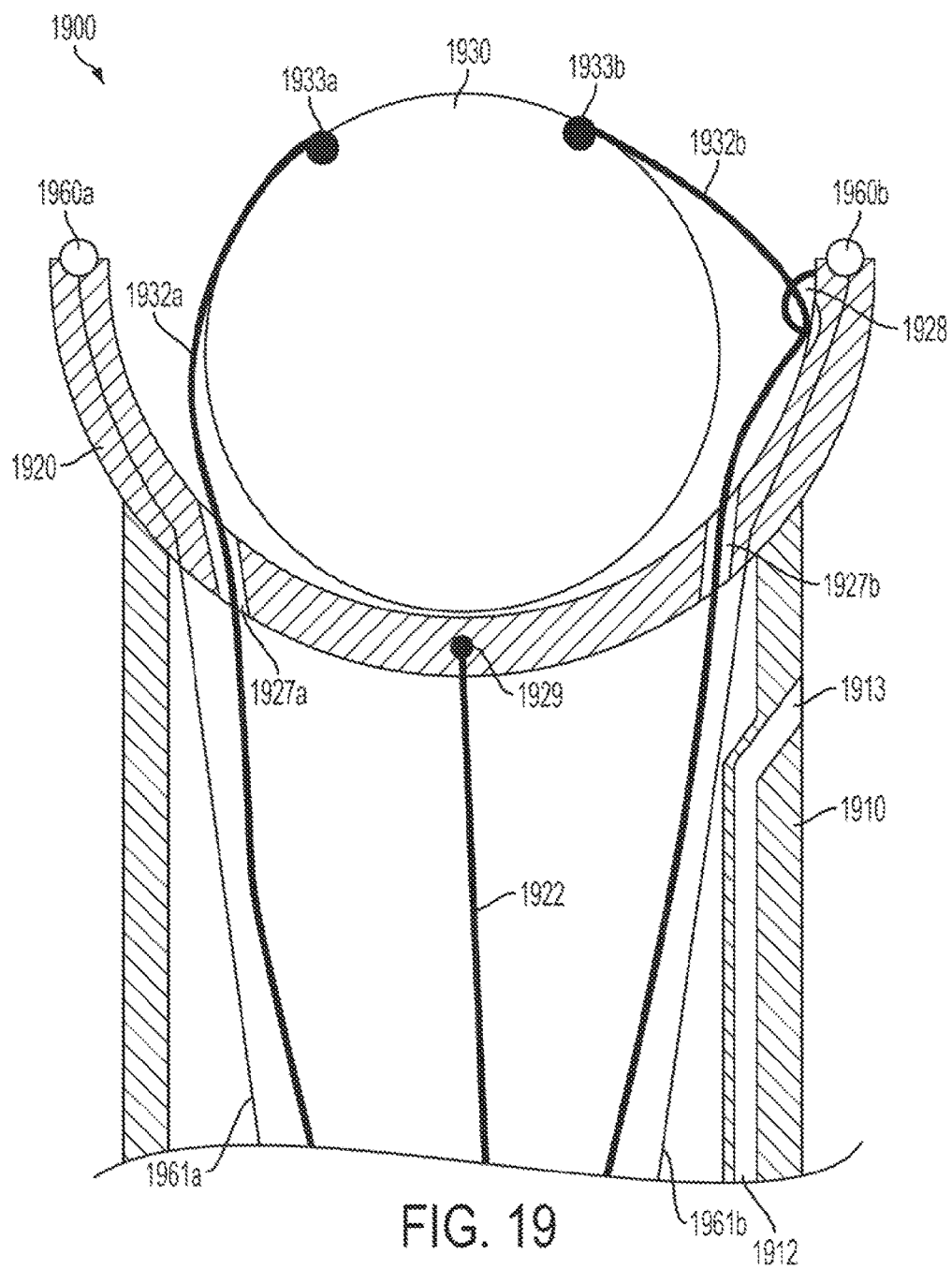
FIG. 19 illustrates various embodiments of a device including a rotatable distal assembly comprising a mechanical advantage element.

FIG. 19 illustrates a side sectional view of a distal portion of an exemplary device. As illustrated by FIG. 19, a device may include an element configured to limit travel of a rotating cable. Device 1900 may include tube 1910, such as a shaft similar to shaft 1510 of FIG. 15A, 15B or 15C, tube 1610 of FIG. 16, or a shaft of the multi-link devices of FIGS. 1 through 14. Positioned at the distal end of tube 1910 may be cup assembly 1920 maintained in longitudinal position by tensioning of cable 1922, which attaches to cup assembly 1920 at weld 1929. Sphere 1930, shown with a smaller diameter than the concave surface of cup assembly 1920, may be attached to two cables, cables 1932a and 1932b at welds 1933a and 1933b respectively. Cables 1932a and 1932b may pass through holes 1927a and 1927b respectively, of cup assembly 1920. Cable 1932b may pass through ring 1928 of cup assembly 1920 such that as cable 1932b is retracted, rotation of sphere 1930 in a clockwise direction is limited to the location where weld 1933b is proximate ring 1928. Application of torsional force to sphere 1930 by retraction of cable 1932a may include a tangential force applied at weld 1933a as well as forces resulting from any frictional engagement of cable 1932a with the surface; of sphere 1930. Application of torsional force to sphere 1930 by retraction of cable 1932b may include torsion created by the force vector between weld 1933b and ring 1928. Numerous configurations of hole 1927a and weld 1933a may be chosen to modify the torsional response of sphere 1930 caused when cable 1932a is retracted. Similarly, numerous positions and other configurations of ring 1928 and weld 1933b may be chosen to customize the torsional response of sphere 1930 caused when cable 1932b is retracted. In an alternative embodiment, a similar ring may be provided for cable 1932a, such that rotation in a counter-clockwise direction can be limited.

Device 1900 may include a flint lumen, lumen 1912 which may exit tube 1910 at exit port 1913. Lumen 1912 may be configured to allow one or more tools to pass out of tube 1910, or to deliver one or more fluid into the area proximate port 1913. Sphere 1930 and cup assembly 1920 include one or more thru holes which may be configured to allow one or more tools to pass through and be rotated by the rotation of sphere 1930, as has been described in detail hereabove. Cup assembly 1920 may include on its distal end, cameras 1960a and 1960b oriented to view the area in front of sphere 1930 as shown, such as to view one or more tools advanced through sphere 1930. Wide angle lenses may be included to view radially out, such as when sphere 1930 and any attached or inserted tools, have been rotated 90°. Cameras 1960a and 1960b may be attached to wires 1961a and 1961b respectively, each of which travels proximally to as handle, such as described in reference to FIG. 15 hereabove. The handle may include a monitor or a video attachment port for connection to a monitor, in an alternative embodiment, cameras 1960a and 1960b may be simply camera lenses and wires 1961a and 1961b may be fiber optic cables operably attached to the lenses such that a camera can be attached to device 1900 and view the image provided by the lenses. The handle may include one or more controls operably connected to cables 1932a and 1932b, as well as cable 1922. The handle may include one or more ports for introduction of one or more tools configured to exit sphere 1930.

Figure 20:
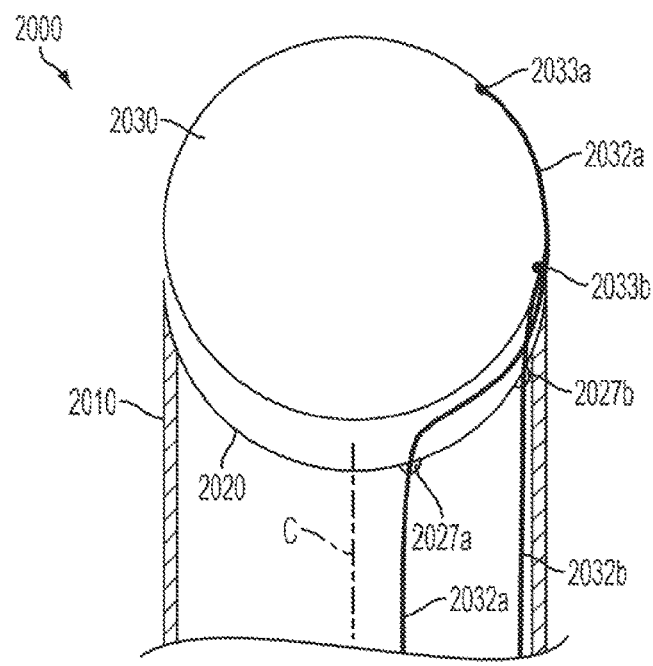
FIG. 20 illustrates various embodiments a device including a first rotating cable and second rotating, cable that provide different rotational performance.

FIG. 20 illustrates a side sectional view of an exemplary distal portion of a device according to an embodiment. As illustrated by FIG. 20, the device may include two cables and associated pass thru holes that are oriented to different rotational performance. Device 2000 may include tube 2010, such as a shaft similar to shaft 1510 of FIG. 15, 15A or 15B, tube 1610 of FIG. 16, or a shaft of the multi-link devices of FIGS. 1 through 14 integral to the distal end of tube 2010 may be concave surface 2020, an adapted link, which may rotatingly mates with the convex surface of sphere 2030. Sphere 2030 may be attached to cable 2032a and 2032b at welds 2933a and 2033b respectively. Cables 2032a and 2032b may pass through convex surface 2020 at holes 2027a and 2027b respectively. The configuration of the holes (e.g. holes 2027a and 2027b) of device 2000 may be such that the closer the hole is located to central axis C of the distal end of tube 2010, the greater the range of rotation is made available by retracting the associated cable. The configuration of the termination points (e.g. welds 2033a and 2033b) may be such that the larger the amount of circumference traversed between the hole and termination point, the greater the range of rotation is made available by retraction the associated cable. Referring back to FIG. 20, hole 2027a through which cable 2032a may pass may be located more proximal to axis C than hole 2027b through which cable 2032b passes through. Also, weld 2033a of cable 2032a and weld 2033b of cable 2032b may be positioned such that cable 2032a traverses more circumference of sphere 2030 than cable 2032a does. Therefore, cable 2032a may have a much larger rotational range (approaching 180°) than cable 2032b does.

Sphere 2030 and concave surface 2020 may include one or more thru holes configured to allow one or more tools to pass through and to be rotated by the rotation of sphere 2030, as has been described in detail hereabove. Device 200 may include at its proximal end a handle such as that described in reference to FIG. 15 hereabove. The handle may include one or more controls operably connected to cables 2032a and 2032b. The handle may include one or more ports for introduction of one Or more tools configured to exit sphere 2030.

Figure 21:
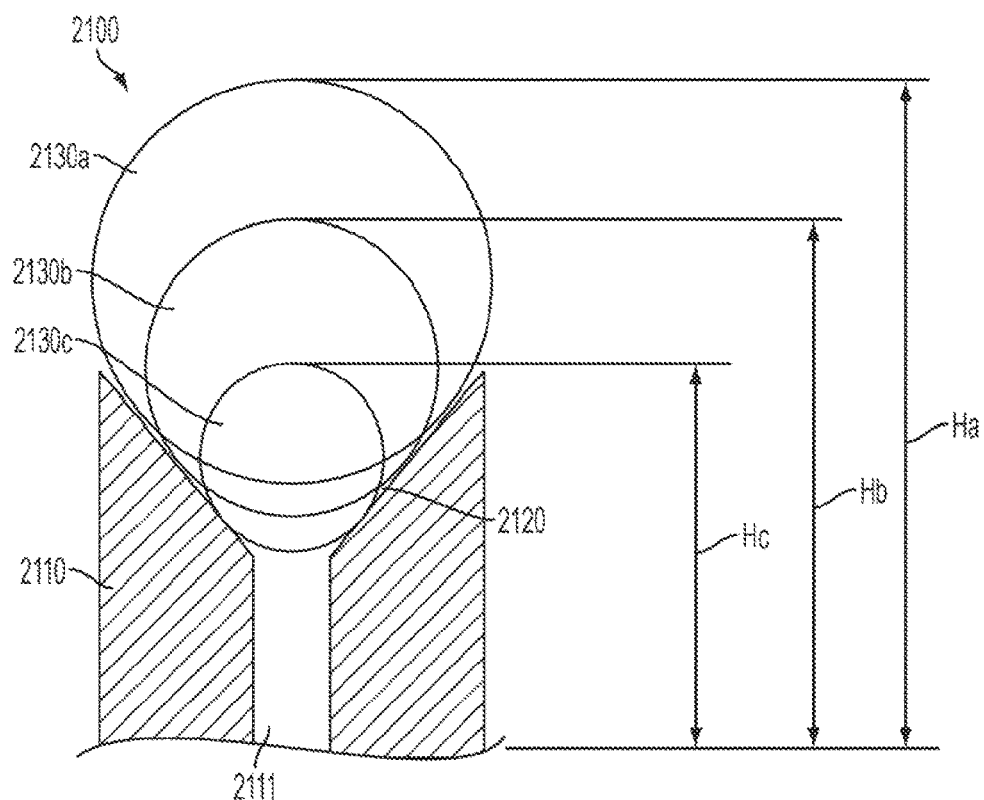
FIG. 21 illustrates various embodiments of a device including multiple rotating, spheres.

FIG. 21 illustrates a side sectional view of an exemplary distal portion of a device. As illustrated by FIG. 21, a device may include a kit of multiple rotating links that can be used with a single adapted link. Device 2100 may include tube 2110, such as a shaft similar to shaft 1510 of FIG. 15, 15A or 15B, tube 1610 of FIG. 16, or a shaft of the multi-link devices of FIGS. 1 through 14. Integral to the distal end of tube 2110 may be a linearly tapered, concave surface, cone surface 2120, an adapted link, which may rotatingly mate with the convex surfaces of spheres 2130a, 2130b and 2130c. Spheres 2130a, 2130b and 2130c may be configured to engagably attach to one or more rotating cables which may pass through charm 2111 or other cable lumen of tube 2110. The engagable attachment may include attachment means such as a loop located at or near the end of one or more cables that attaches to a threaded hole of a sphere with a screw, as barb or other projection which frictionally engages a hole in a sphere or other user engagable cable attachment means.

Spheres 2130a, 2130b and 2130c may have decreasing diameters, respectively, and may have unique engaging surface areas, each a circle (e.g. a single line, of contact), with linear tapered conical surface 2120. The varied diameters may cause spheres 2130a, 2130b and 2130c to be positioned at different longitudinal positions along conical surface 2120, heights H1, H2 and H3 respectively. The forces required to actuate the sphere (with one or more cables not shown but described in detail hereabove) may vary due to the change in moment arm between each cable and sphere. The surface area of engagement and frictional forces may allow customized rotational movement and forces required. Alternatively and/or additionally, the conical features of conical surface 2120 may be varied, in diameter and angle of taper (i.e. pitch), to customize range of motion as well as forces required and generated from and by retraction and advancement of one or more cables. In an embodiment, the cross-sectional geometry of a sphere or conical surface may be varied to customize performance and/or forces required.

Spheres 2130 and cone surface 2120 may include one or more thru holes which may be configured to allow one or more tools to pass through and be rotated by the rotation of spheres 2130 as has been described in detail hereabove. Device 2100 may include a handle at its proximal end such as described in reference to FIG. 15 hereabove. The handle may include one or more controls operably connected to one or more cables, which may terminate at spheres 2130 and which may be configured to rotate spheres 2130 as has been described, in detail hereabove. The handle may include one or more ports for introduction of one or more tools configured to exit sphere 2130.

While the positioning of cable exit holes and cable termination points as shown in FIG. 20 and FIG. 21 imply that larger rotations can be achieved with holes close to the center axis of the adaptive link and/or termination locations "higher up in altitude" on the rotating link. There are limitations in having multiple cables positioned for a maximum range or rotation, such as increasing the likelihood of for singularities and other non-desired rotational states (e.g. loss of control of the rotating link).

It should be understood that numerous other configurations of the devices, systems and methods described herein can be employed without departing from the spirit and scope of this application. Numerous figures have illustrated typical dimensions, but it should be understood that other dimensions can be employed which result in similar functionality and performance.

The described devices and systems may be used to perform various procedures including medical procedures such as diagnostic procedures, therapeutic procedures, surgery, blunt dissections, minimally invasive surgery, interventional procedures, endoscopic procedures and/or the like. In an embodiment, the described devices and systems may be used to perform a procedure on an organ of a patient, such as the heart during a cardiac ablation or mapping procedure for a patient diagnosed with a heart arrhythmia.

The elongate shafts of a device may have various cross-sectional geometries including geometries that vary along the length of the shaft. Applicable cross-sectional geometries include, but are not limited to, circular, elliptical, trapezoidal, rectangular, triangular and/or other geometries.

While the distal rotating links have been illustrated at the distal portion of the described devices and systems, the distal rotating links may be located at the proximal end or at an intermediate portion of the device, such as when the device includes multiple links attached to the distal end of the distal rotating link, allowing these multiple links and any tools passed within or attached thereto to be rotated by rotating the distal rotating link.

In an embodiment, adaptive links may be fixedly or removably attached to the elongate tube and may utilize one or more attachment means. The adaptive links may be fixedly attached to the elongate shaft in a kinematically constrained manner, such as with one or more cables, one or more of these cables further configured to cause rotation of the adaptive link. In an embodiment, the adaptive link may be fixedly attached to the elongate tube with a hinge pin arrangement, such that the attachment is independent of rotating cable tension. The adaptive links may have relatively concave or convex distal ends, configured to allow rotation of the mating, surface of the associated rotating link. Relative diameters of the mating surfaces may be similar or dissimilar.

The rotating links may be oriented in various orientations such as a change in orientation of 90° to 180°. The rotating links may be operated in a reciprocating motion, and the motion of the rotating link may be used to actuate a tool such as a surgical tool or an end effector tool integral to the rotating link.

The shafts, adapted links and rotating links may include one or more exit holes from which one or more tools may exit the device. A system may include multiple shafts, adaptive links and/or rotating links, such as components with different working channel or other thru hole sizes and pattern, different exit ports from which one or more tools may exit; different cable termination types and/or locations; different integral tools such as one or more cameras or other tools integral to a rotating link; and other differences that may be supplied in a system of kit form. The shafts, adapted links and rotating links may include a tool attachment element configured to attach one or more tools thereto.

The described systems and devices may include one or more rotating or attachment cables. In an embodiment, three or more rotating cables may be included such as to provide stability, and two degree of freedom rotation (pitch and yaw), such as when the rotating link includes a complete spherical surface. One or two cables may be used such as when the rotating link is constrained by mating projections and grooves, or by other motion constraining means. A first cable may be used to cause rotation in a first direction or pattern, and a second cable used to return the rotating link to its original position. In an embodiment, three or more attachment cables may be included to kinematically constrain the adaptive link, such as to provide stability and allow rotation of the adaptive link with two degrees of freedom.

The cables may be similar or dissimilar, and may provide additional functions such as to transmit energy; allow flow of liquids or gases such as cryogenic materials to ablate tissue; and provide additional functions. The cables may be solid, or include one or more lumens, such as a lumen configured to transport a liquid or gas, such as a cryogenic material used to perform a tissue ablation procedure, or a cooling fluid used to prevent overheating of tissue of a patient. One or more cables may be stretch resistant, such as a cable made of metal wire or hypotube such as a stainless steel or Nitinol wire, fluorocarbon filament, braided strands of material and/or the like. One or more cables may be configured to stretch, such as a cable made of a monofilament polymer or monofilament polymer blend.

In an embodiment, the described methods may include the performance of medical and other procedures. In an embodiment, a medical procedure may be performed by a clinician and may include a diagnostic procedure, a therapeutic procedure, a blunt dissection, surgery, minimally invasive surgery, an interventional procedure, an endoscopic procedure and/or the like. Methods may include various rotations of the rotating link, such as 90° and 180° rotations. In an embodiment, the rotating link may be rotated approximately 90° or otherwise such that a tool can be advanced orthogonally toward the surface of tissue such as esophageal tissue or colorectal tissue, when the device is inserted into the esophagus or rectum, respectively. In an embodiment, the rotating link may be rotated to actuate one or more tools, such as a surgical tool that passes thru the rotating link, or a tool attached to the rotating link, such as an end effector tool. Motion of the rotating link may be a reciprocating motion, such as to cause a blunt or sharp tool to cut or dissect tissue. The various links of the described devices may be locked in place by the tensioning of one or more cables. In an embodiment, one or more links may be locked prior to rotation of the rotating link and/or advancement of one or more tools through the rotating link.

While several embodiments of the invention have been described herein by way of example, those skilled in the art will appreciate that various modifications, alterations, and adaptations to the described embodiments may be realized without departing from the spirit and scope of the invention defined by the appended claims.

What is claimed is:

1. A system comprising:
    an elongate tube comprising a lumen that extends from a proximal end of the elongate tube to a distal end of the elongate tube, wherein one or more rotation cables are positioned in the lumen, wherein the distal end of the elongate tube comprises a linearly tapered conical surface; and
    a kit comprising a plurality of spherical rotating links, wherein each of the spherical rotating links comprises a mating surface configured to interface with the conical surface, wherein each of the spherical rotating links has a different diameter, wherein each of the spherical rotating links is configured to be positioned at a different longitudinal position along the conical surface, wherein each of the spherical rotating links is configured to connect to one or more of the rotation cables.

2. The system of claim 1, wherein the conical surface is concave.

3. The system of claim 1, wherein:
    at least one of the spherical rotating links comprises a threaded hole,
    one or more of the rotation cables comprises a loop located near an end of the rotation cable, wherein the loop is configured to be connected to the threaded hole via a connector.

4. The system of claim 1, wherein the conical surface comprises one or more through holes.

5. The system of claim 1, wherein one or more of the spherical rotating links comprises one or more through holes.

6. The system of claim 1, wherein:
    at least one of the spherical rotating links comprises one or more through holes,
    one or more tools pass through at least one of the one or more through holes, wherein rotation of the at least one spherical rotating link causes rotation of the one or more tools.

7. The system of claim 1, wherein the elongate tube comprises a multi-linked device.

8. A system, comprising:
    an elongate tube comprising a lumen that extends from a proximal end of the elongate tube to a distal end of the elongate tube, wherein one or more rotation cables are positioned in the lumen;
    a spherical distal link cup connected to a distal end of the elongate tube, wherein the spherical distal link cup comprises a concave surface,
    a kit comprising a plurality of spherical rotating links, wherein each of the spherical rotating links comprise a mating surface, wherein each of the spherical rotating links has a different diameter, wherein each of the spherical rotating links is configured to be positioned a different longitudinal position along the concave surface, wherein each of the spherical rotating links is configured to connect to one or more of the rotation cables.

9. The system of claim 8, wherein the spherical distal link cup rotatably engages with the mating surface of at least one of the spherical rotating links.

10. The system of claim 8, wherein:
    at least one of the spherical rotating links comprises a threaded hole,
    one or more of the rotation cables comprises a loop located near an end of the rotation cable, wherein the loop is configured to be connected to the threaded hole via a connector.

11. The system of claim 8, wherein the spherical distal link cup comprises one or more through holes.

12. The system of claim 8, wherein one or more of the spherical rotating links comprises one or more through holes.

13. The system of claim 8, wherein:
    at least one of the spherical rotating links comprises one or more through holes,
    one or more tools are configured to pass through at least one of the one or more through holes, wherein rotation of the at least one spherical rotating link causes rotation of the one or more tools.

14. The system of claim 8, wherein the elongate tube comprises a multi-linked device.

* * * * *